US010058593B2

(12) United States Patent
Kidron

(10) Patent No.: US 10,058,593 B2
(45) Date of Patent: Aug. 28, 2018

(54) METHODS AND COMPOSITIONS FOR ORAL ADMINISTRATION OF PROTEINS

(75) Inventor: Miriam Kidron, Jerusalem (IL)

(73) Assignee: Oramed Ltd., Jerusalem (IL)

( * ) Notice: Subject to any disclaimer, the term of this patent is extended or adjusted under 35 U.S.C. 154(b) by 355 days.

(21) Appl. No.: 12/934,754

(22) PCT Filed: Feb. 26, 2009

(86) PCT No.: PCT/IL2009/000223
§ 371 (c)(1),
(2), (4) Date: Sep. 27, 2010

(87) PCT Pub. No.: WO2009/118722
PCT Pub. Date: Oct. 1, 2009

(65) Prior Publication Data
US 2011/0014247 A1 Jan. 20, 2011

Related U.S. Application Data

(60) Provisional application No. 61/064,779, filed on Mar. 26, 2008.

(51) Int. Cl.
A61K 47/10 (2017.01)
A61K 38/22 (2006.01)
A61K 38/28 (2006.01)
A61K 45/06 (2006.01)
A61K 38/56 (2006.01)
A61K 38/57 (2006.01)
A61K 35/60 (2006.01)

(52) U.S. Cl.
CPC .......... *A61K 38/2278* (2013.01); *A61K 35/60* (2013.01); *A61K 38/28* (2013.01); *A61K 38/56* (2013.01); *A61K 38/57* (2013.01); *A61K 45/06* (2013.01)

(58) Field of Classification Search
None
See application file for complete search history.

(56) References Cited

U.S. PATENT DOCUMENTS

| 4,579,730 | A | 4/1986 | Kidron et al. |
| 5,034,415 | A | 7/1991 | Rubin |
| 5,206,219 | A | 4/1993 | Desai |
| 5,665,700 | A | 9/1997 | Cho et al. |
| 5,824,638 | A | 10/1998 | Burnside et al. |
| 6,525,102 | B1 | 2/2003 | Chen et al. |
| 6,692,766 | B1 | 2/2004 | Rubinstein et al. |
| 6,761,903 | B2 | 7/2004 | Chen et al. |
| 6,858,576 | B1 | 2/2005 | Young et al. |
| 7,404,973 | B2 | 7/2008 | Konwinski et al. |
| 9,186,412 | B2 | 11/2015 | Kidron et al. |
| 9,259,456 | B2 | 2/2016 | Kidron |
| 2002/0032171 | A1 | 3/2002 | Chen et al. |
| 2003/0118610 | A1 | 6/2003 | Stern et al. |
| 2004/0097410 | A1 | 5/2004 | Zheng et al. |
| 2005/0143303 | A1 | 6/2005 | Quay et al. |
| 2005/0232981 | A1 | 10/2005 | Ben-Sasson |
| 2006/0018874 | A1 | 1/2006 | Radhakrishnan et al. |
| 2006/0045868 | A1 | 3/2006 | Meezan et al. |
| 2006/0045869 | A1 | 3/2006 | Meezan et al. |
| 2006/0234913 | A1 | 10/2006 | Arbit et al. |
| 2006/0264401 | A1 | 11/2006 | Campbell et al. |
| 2006/0286129 | A1 | 12/2006 | Sarubbi |
| 2006/0293232 | A1 | 12/2006 | Levy et al. |
| 2007/0077283 | A1 | 4/2007 | Quay et al. |
| 2007/0086972 | A1 | 4/2007 | Birnbaum |
| 2007/0087957 | A1 | 4/2007 | Kidron |
| 2008/0274203 | A1 | 11/2008 | Bruheim et al. |
| 2009/0312302 | A1 | 12/2009 | Currie |
| 2011/0046053 | A1 | 2/2011 | Kidron |
| 2011/0092510 | A1 | 4/2011 | Klein et al. |
| 2011/0092592 | A1 | 4/2011 | Yano |
| 2011/0105510 | A1 | 5/2011 | Ishikawa |
| 2011/0142800 | A1 | 6/2011 | Kidron et al. |
| 2011/0166062 | A1 | 7/2011 | DiMarchi et al. |
| 2011/0166228 | A1 | 7/2011 | Holmeide et al. |
| 2011/0275561 | A1 | 11/2011 | Graefe-Mody et al. |
| 2012/0009259 | A1 | 1/2012 | Delaet et al. |
| 2012/0122940 | A1 | 5/2012 | Hovland et al. |
| 2012/0165251 | A1 | 6/2012 | Klein et al. |
| 2012/0202849 | A1 | 8/2012 | Pareek |
| 2012/0264824 | A1 | 10/2012 | Mizuguchi et al. |
| 2013/0195939 | A1 | 8/2013 | Kidron |
| 2013/0273154 | A1 | 10/2013 | Fayad et al. |

(Continued)

FOREIGN PATENT DOCUMENTS

| CA | 1223200 A | 6/1987 |
| CA | 2621577 A1 | 3/2007 |

(Continued)

OTHER PUBLICATIONS

Agarwal, et al.; "Oral Delivery of Proteins: Effect of Chicken and Duck Ovomucoid on the Stability of Insulin in the Presence of α-Chymotrypsin and Trypsin"; Pharm. Pharmacol. Commun.; (2000); 6: 223-227.

Carino, et al.; "Oral insulin delivery"; Advanced Drug Delivery Review (1999); 35: 249-257.

Cournarie, et al.; "Insulin-loaded W/O/W multiple emulsions: comparison of the performances of systems prepared with medium-chain-triglycerides and fish oil"; Euro. J. of Pharmaceutics and BioPharmaceutics; (2004); 58(3): 477-482.

Hays, et al.; "Prevention and Treatment of Type 2 Diabetes: Current Role of Lifestyle, Natural Product, and Pharmacological Interventions"; Pharmacol. Ther. (2008); 118(2): 181-191.

Iyer, et al.; "Oral insulin—a review of current status"; Diabetes, Obesity and Metabolism (2010); 12: 179-185.

(Continued)

*Primary Examiner* — Hope Robinson
(74) *Attorney, Agent, or Firm* — Sterne, Kessler, Goldstein & Fox P.L.L.C.

(57) ABSTRACT

This invention provides compositions that include a protein and at least two protease inhibitors, method for treating diabetes mellitus, and methods for administering same, and methods for oral administration of a protein with an enzymatic activity, including orally administering same.

46 Claims, 3 Drawing Sheets

(56) References Cited

U.S. PATENT DOCUMENTS

| | | | |
|---|---|---|---|
| 2014/0220134 | A1 | 8/2014 | Zierhut et al. |
| 2014/0377344 | A1 | 12/2014 | Hershko et al. |
| 2015/0017238 | A1 | 1/2015 | Kidron |
| 2015/0335715 | A1 | 11/2015 | Kidron et al. |
| 2016/0206703 | A1 | 7/2016 | Kidron |

FOREIGN PATENT DOCUMENTS

| | | |
|---|---|---|
| CN | 101095942 A | 2/2008 |
| EP | 0351651 A2 | 1/1990 |
| IL | 68769 A | 2/1986 |
| JP | 02-250823 | 10/1990 |
| JP | 09-208485 A | 8/1997 |
| JP | 10-330287 A | 12/1998 |
| JP | 00-050793 A | 2/2000 |
| JP | 2001-240558 | 4/2001 |
| JP | 2001-240558 A | 9/2001 |
| JP | 2005-525308 A | 8/2005 |
| JP | 2011-515458 A | 5/2011 |
| KR | 01/0069322 A | 7/2001 |
| KR | 01-0069433 A | 7/2001 |
| RU | 2104715 C1 | 2/1998 |
| WO | WO 91/14454 A1 | 10/1991 |
| WO | WO 97/03688 | 2/1997 |
| WO | WO 00/24424 A1 | 7/2000 |
| WO | WO 2003/057170 A2 | 7/2003 |
| WO | WO 2007/029238 | 3/2007 |
| WO | WO 09/118722 A2 | 10/2009 |
| WO | WO 2009/136392 A2 | 11/2009 |
| WO | WO 2011/082338 A1 | 7/2011 |

OTHER PUBLICATIONS

Lasserson, et al.; "Optimal insulin regimens in type 2 diabetes mellitus: systematic review and meta-analyses"; Diabetologia (2009); 52: 1990-2000.

Li and Deng; "Oil-based formulation for oral delivery of insulin"; J. Pharmacy Pharmacol 2004; 56: 1101-1107.

Onuki, et al.; "In vivo effects of highly purified docosahexaenoic acid on rectal insulin absorption"; Int. J. of Pharmaceutics; (2000); 198(2): 147-156.

Silva-Cunha et al.; "W/O/W multiple emulsions of insulin containing a protease inhibitor and an absorption enhancer: preparation, characterization and determination of stability towards proteases in vitro"; Int. J. of Pharmaceutics; (1997); 158(1): 79-89.

Bar-On, H., et al.; "Enteral Administration of Inslin in the Rat"; Br. J. Pharmac. (1981); 73: 21-24.

Cernea, et al.; "Dose-Response Relationship of Oral Insulin Spray in Healthy Subjects"; Diabetes Care (2005); 28(6): 1353-1357.

Cernea, et al.; "Dose-Response Relationship of an Oral Insulin Spray in Six Patients with Type 1 Diabetes: A Single-Center, Randomized, Single-Blind, 5-Way Crossover Study"; Clinical Therapeutics (2005); 27(10): 1562-1570.

Cernea, et al.; "Comparison of pharmacokinetic and pharmacodynamic properties of single-dose oral insulin spray and subcutaneous insulin injection in healthy subjects using the euglycemic clamp technique"; Clinical Therapeutics (2004); 26(12): 2084-2091.

Kidron, et al.; "A novel per-oral insulin formulation: proof of concept study in non-diabetic subjects"; Diabetic Medicine (2004); 21: 354-357.

Nissan, et al.; "Intestinal absorption of low molecular weight heparin in animals and human subjects"; Haemostasis (2000); 30: 225-232.

Ziv, et al.; "Oral administration of insulin in solid form to nondiabetic and diabetic dogs"; Journal of Pharmaceutical Sciences (1994); 83(6): 792-794.

Cole, et al.; "Challenges and opportunities in the encapsulation of liquid and semi-solid formulations into capsules for oral administration"; Advanced Drug Delivery Reviews (2008); 60: 747-756.

Er-Il, et al.; "In vitro and in vivo evaluation of a novel oral insulin formulation"; Acta Pharmacologica Sinica (2006); 27(10): 1382-1388.

Maher, S. et al.; "Safety and efficacy of sodium caprate in promoting oral drug absorption: from in vitro to the clinic"; Advanced Drug Delivery Reviews; (2009); 61: 1427-1449.

Bendayan, et al.; "Morpho-cytochemical and biochemical evidence for insulin absorption by the rat ileal epithelium"; Diabetologia (1990); 33: 197-204.

Bendayan, et al.; "Biochemical and morpho-cytochemical evidence for the intestinal absorption of insulin in control and diabetic rats. Comparison between the effectiveness of duodenal and colon mucosa"; Diabetologia (1994); 37: 119-126.

Raz, et al.; "Rectal Administration of Insulin"; Israel Journal of Medical Sciences (1984); 20: 173-175.

Ziv, et al.; "Bile Salts Promote the Absorption of Insulin from the Rat Colon"; Life Sciences (1981); 29: 803-809.

Ziv, et al.; "Absorption of Protein via the Intestinal Wall A Quantitative Model"; Biochemical Pharmacology (1987); 36(7): 1035-1039.

Gowthamarajan & Kulkarni; Oral Insulin—Fact or Fiction—Possibilities of Achieving Oral Delivery for Insulin; Resonance (2003); 38-46.

Heine, et al.; "Exenatide versus Insulin Glargine in Patients with Suboptimally Controlled Type 2 Diabetes"; American College of Physicians—Annals of Internal Medicine 2005; 143(8): 559-569.

Kidron, et al.; "Extended exposure to an oral insulin formulation yields decreased insulin secretion in Type II diabetes subjects"; Diabetes Technology Meeting Nov. 11-13, 2010.

Mack, et al. "Antiobestiy action of peripheral exenatide (exendin-4) in rodents: effects on food intake, body weight, metabolic status and side-effect measures"; International Journal of Obesity (2006); 30: 1332-1340.

Miyagawa, Jun-ichiro; Med Sci Digest 2008 34(4):147-150.

Morishita, et al.; "Hypoglycemic effect of novel oral microspheres of insulin with protease inhibitor in normal and diabetic rats"; Int. J. of Pharma; (1992); 78: 9-16.

Ray Dirks Research; "Novo Nordisk Sitting on $2 Billion in Cash May Look to Acquire Oramed or ISIS for Oral Insulin"; May 31, 2012.

Sherman, "Oramed Enrolls First Patient in its Phase 2a U.S. Oral Insulin Clinical Trial"; Jul. 8, 2013.

[No Author Listed] Sigma-Aldrich. 2017. T9128. Trypsin inhibitor from Glycine max (soybean). (retrieved from www.sigmaaldrich.com/catalog/product/sigma/t9128?lang+en®ion=US).

[No Author Listed], What Makes a Supplement "Pharmaceutical Grade"?, Doctors Supplement Store, Dec. 14, 2015, (retrieved from http://www.doctorssupplementstore.com/what-makes-a-supplement-pharmaceutical-grade/ [last accessed Sep. 29, 2017], pp. 1-2.).

Bernkop-Schnurch et al., Synthesis and In Vitro Evaluation of Chitosan-EDTA-Protease-Inhibitor Conjugates Which Might Be Useful in Oral Delivery of Peptides and Proteins. Pharmaceutical Research. 1998;15(2):263-9.

Bernkop-Schnurch et al., Development and In Vitro Evaluation of a Drug Delivery System based on Chitosan-EDTA BBI Conjugate. Journal of Drug Targeting. 1998;6(3):207-214.

Bernkop-Schnurch, The use of inhibitory agents to overcome the enzymatic barrier to perorally administered therapeutic peptides and proteins. Journal of Controlled Release. 1998;52:1-16.

Krauland et al., Oral insulin delivery: the potential of thiolated chitosan-insulin tablets on nondiabetic rats. Journal of Controlled Release. 2004;95:547-555.

Kunitz et al., Crystalline soybean trypsin inhibitor : II. General Properties. J Gen Physiol. Mar. 20, 1947;30(4):291-310.

Marschutz et al., Oral peptide drug delivery: polymer-inhibitor conjugates protecting insulin from enzymatic degradation in vitro. Biomaterials. 2000;21:1499-1507.

Morishita et al. Novel oral microspheres of insulin with protease inhibitor protecting from enzymatic degradation. Int J Pharm. 1992;78:1-7.

Nadeau et al., Treatment of non-alcoholic fatty liver disease with metformin versus lifestyle intervention in insulin-resistant adoles-

(56) References Cited

OTHER PUBLICATIONS cents. Pediatr Diabetes. Feb. 2009;10(1):5-13. Doi: 10.1111/j.1399-5448.2008.00450.x. Epub Aug. 20, 2008.
Park et al., Oral protein delivery: Current status and future prospect. Reactive and Functional Polymers. 2011;71:280-287.
Park et al., Characterization of human insulin microcrystals and their absorption enhancement by protease inhibitors in rat lungs. International Journal of Pharmaceutics. 2007;339:205-212.
Shyangdan et al., Insulin sensitisers in the treatment of non-alcoholic fatty liver disease: a systematic review. Health Technol Assess. Nov. 2011;15(38):1-110. doi: 10.3310/hta15380.
Excerpted prosecution history, U.S. Appl. No. 11/513,343 (now U.S. Pat. No. 9,259,456 B2), Kidron, M., Sep. 14, 2006 to Jan. 27, 2016.
Excerpted prosecution history, U.S. Appl. No. 13/058,259 (now U.S. Pat. No. 9,186,412 B2), Kidrion, M. et al., Feb. 9, 2011 to Oct. 28, 2015.
Excerpted prosecution history, U.S. Appl. No. 13/855,346, Kidron, M., Apr. 2, 2013 to Jul. 14, 2017.
Excerpted prosecution history, U.S. Appl. No. 14/370,452, Kidron, M., Jul. 2, 2014 to Dec. 4, 2017.
Excerpted prosecution history, U.S. Appl. No. 14/996,800, Kidron, M., Jan. 15, 2016 to Nov. 8, 2017.
Communication pursuant to Article 94(3) EPC for EP Appl. No. 09 725 603.6-1455, dated Sep. 15 2017, European Patent Office, Rijswijk, Netherlands.
Requisition by the Examiner in Accordance with Subsection 30(2) of the Patent Rules, for CA Appl. No. 2,719,272, dated Aug. 31, 2017, Canadian Intellectual Property Office, Gatineau, Quebec.
International Preliminary Report on Patentability for PCT/IL2009/000223 dated Sep. 28, 2010.
[No Author Listed] Cure Talk (retrieved from http://trialx.com/curetalk/2012/05/type-2-diabetes-difficult-to-treat-in-children-new-study/ on Apr. 22, 2015, 2 pages).
[No Author Listed] Joslin Diabetes Center (retrieved from http://www.joslin.org/info/will_diabetes_go_away.html on Apr. 22, 2015, 2 pages).
[No Author Listed] The Observer (retrieved from http://observer.com/2014/02/tough-to-swallow-paper-trail-breakthrough-leads-to-penny-stock-profiteers/ on Apr. 22, 2015, 5 pages).
[No Author Listed] WebMD (retrieved from http://www.webmd.com/diabetes/is-there-cure on Apr. 22, 2015, 3 pages).
[No Author Listed] Worthington Biochemical Corporation (2016; Trypsin inhibitors C.A.S.: 9035-81-1. On the web at worthington-biochem.com/TI/default.html.
Birk, Trypsin and chymotrypsin inhibitors from soybeans.Methods Enzymol. 1976;45:700-7.
Chiquette et al., Treatment with exenatide once weekly or twice daily for 30 weeks is associated with changes in several cardiovascular risk markers. Vasc Health Risk Manag. 2012;8:621-9. doi: 10.2147/VHRM.S37969. Epub Nov. 12, 2012.
Eldor et al., A Single-Blind, Two-Period Study to Assess the Safety and Pharmacodynamics of an Orally Delivered GLP-1 Analog (Exenatide) in Healthy SubjectsAmerican Diabetes Association 70th Annual Scientific Sessions, Jun. 25-29, 2010A, Orlando, Florida.
Eldor et al., Open-label study to assess the safety and pharmacodynamics of five oral insulin formulations in healthy subjects.Diabetes Obes Metab. Mar. 2010;12(3):219-23. doi: 10.1111/j.1463-1326.2009.01153.x.
Eldor et al., Novel glucagon-like peptide-1 analog delivered orally reduces postprandial glucose excursions in porcine and canine models. J Diabetes Sci Technol. Nov. 1, 2010;4(6):1516-23.
Gershanik et al., Selfdispersing lipid formulations for improving oral absorption of lipophilic drugs. European Journal of Pharmaceuticals and Biopharmaceutics. 2000;50:179-188.
Griffin, Calculation of HLB Values of Non-Ionic Surfactants. J Soc Cosmetic Chemists 5:259 (1954).
Koide et al., Studies on soybean trypsin inhibitors. 3. Amino-acid sequences of the carboxyl-terminal region and the complete amino-acid sequence of soybean trypsin inhibitor (Kunitz).Eur J Biochem. Feb. 1, 1973;32(3):417-31.
Koide et al., The amino acid sequence of soybean trypsin inhibitor. J. Biochem. 1972;71:165-7.
Martinez-Colubi et al., Switching to darunavir/ritonavir monotherapy (DRV/r mx): effect on kidney function and lipid profile. J Int AIDS Soc. Nov. 11, 2012;15(6):18348. doi:10.7448/IAS.15.6.18348.
Miyashita et al., Hepatoprotective effect of tamoxifen on steatosis and non-alcoholic steatohepatitis in mouse models. J Toxicol Sci. 2012;37(5):931-42.
Ozawa et al., The reactive site of trypsin inhibitors.J Biol Chem. Sep. 10, 1966;241(17):3955-61.
Ryan et al., Assessment of the severity of hypoglycemia and glycemic lability in type 1 diabetic subjects undergoing islet transplantation. Diabetes. Apr. 2004;53(4):955-62.
Siepmann et al., Blends of aqueous polymer dispersions used for pellet coating: importance of the particle size. J Control Release. Jul. 20, 2005;105(3):226-39.
Sprecher et al., Molecular cloning, expression, and partial characterization of two novel members of the ovalbumin family of serine proteinase inhibitors. J Biol Chem. Dec. 15, 1995;270(50):29854-61.
Sun et al., Gene structure, chromosomal localization, and expression of the murine homologue of human proteinase inhibitor 6 (PI-6) suggests divergence of PI-6 from the ovalbumin serpins. J Biol Chem. Jul. 7, 1995;270(27):16089-96.
Tesauro et al., Effects of GLP-1 on forearm vasodilator function and glucose disposal during hyperinsulinemia in the metabolic syndrome. Diabetes Care. Mar. 2013;36(3):683-9. doi: 10.2337/dc12-0763. Epub Oct. 15, 2012.
Umezawa, Structures and activities of protease inhibitors of microbial origin. Methods Enzymol. 1976;45:678-95.
Yeboah et al., A rapid purification method for soybean Bowman-Birk protease inhibitor using hydrophobic interaction chromatography. Protein Expression and Purification. 1996;7:309-14.
PCT/IL2009/000223, dated Sep. 28, 2010, International Preliminary Report on Patentability.
U.S. Appl. No. 14/996,800, filed Jan. 15, 2016 Kidron.
U.S. Appl. No. 13/855,346, filed Apr. 2, 2013, Kidron.
U.S. Appl. No. 14/370,452, filed Jul. 2, 2014, Kidron.
U.S. Appl. No. 14/376,292, filed Aug. 1, 2014, Hershko.
U.S. Appl. No. 14/759,060, filed Jul. 2, 2015, Kidron.

METHODS AND COMPOSITIONS FOR ORAL ADMINISTRATION OF PROTEINS

This application is a 35 U.S.C. 371 National Phase Application of International Application No. PCT/IL2009/000223, filed Feb. 26, 2009, which claims priority from U.S. Provisional Patent Application No. 61/064,779, filed Mar. 26, 2008.

FIELD OF INVENTION

This invention provides oral compositions comprising a protein and at least two protease inhibitors and a method for administering same.

BACKGROUND OF THE INVENTION

Due to improved biotechnology, the accessibility of biologically active peptides to the pharmaceutical industry has increased considerably. However, a limiting factor in the development of peptide drugs is the relative ineffectiveness when given perorally. Almost all peptide drugs are parenterally administered, although parenterally administered peptide drugs are often connected with low patient compliance.

Insulin is a medicament used to treat patients suffering from diabetes, and is the only treatment for insulin-dependent diabetes mellitus. Diabetes Mellitus is characterized by a pathological condition of absolute or relative insulin deficiency, leading to hyperglycemia, and is one of the main threats to human health in the 21st century. The global figure of people with diabetes is set to rise to 220 million in 2010, and 300 million in 2025. Type I diabetes is caused primarily by the failure of the pancreas to produce insulin. Type II diabetes, involves a lack of responsiveness of the body to the action of insulin.

Approximately 20%-30% of all diabetics use daily insulin injections to maintain their glucose levels. An estimated 10% of all diabetics are totally dependent on insulin injections.

Currently, the only route of insulin administration is injection. Daily injection of insulin is causes considerable suffering for patients. Side effects such as lipodystrophy at the site of the injection, lipatrophy, lipohypertrophy, and occasional hypoglycemia are known to occur. In addition, subcutaneous administration of insulin does not typically provide the fine continuous regulation of metabolism that occurs normally with insulin secreted from the pancreas directly into the liver via the portal vein.

The present invention addresses the need for an alternate solution for administration of insulin.

SUMMARY OF THE INVENTION

This invention provides, in one embodiment, a composition comprising a protein or a combination of proteins having a molecular weight of up to 100,000 Daltons and a first protease inhibitor and a second protease inhibitor.

In another embodiment, the present invention provides a method for oral administration of a protein having a molecular weight up to 100,000 Daltons to a subject, whereby a substantial fraction of the protein retains its activity after absorption, through an intestinal mucosal barrier of a subject, comprising administering orally to a subject a pharmaceutical composition comprising the protein and a first protease inhibitor and a second protease inhibitor.

In another embodiment, the present invention provides a method for treating diabetes mellitus in a subject, comprising administering orally to a subject a pharmaceutical composition comprising insulin, Exenatide, or a combination thereof and a first protease inhibitor and a second protease inhibitor, thereby treating diabetes mellitus.

BRIEF DESCRIPTION OF THE DRAWINGS

In FIG. 1 A-C blood glucose levels were significantly reduced in human subjects treated with formulation (3) (8 mg insulin, 150 mg EDTA, 150000 KIU Aprotinin, 125 mg SBTI in 1 ml fish oil in a soft-gel capsule (SwissCup).

DETAILED DESCRIPTION OF THE INVENTION

Figure 1A:
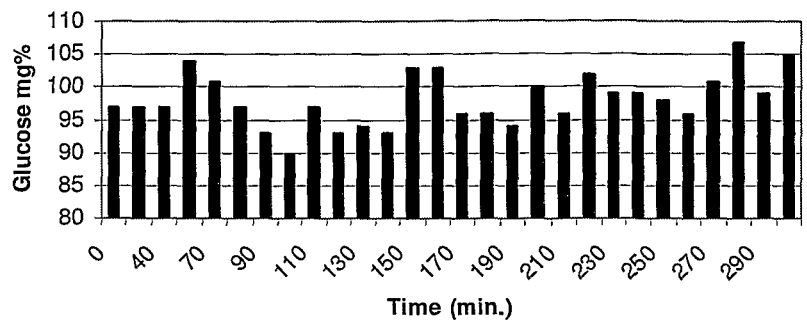
FIG. 1 is a set of bar graphs showing the changes in blood glucose levels after treatment with the formulations of the invention.
FIG. 1D-F shows that total blood insulin was significantly higher especially between 220-300 minutes in human subjects treated with formulation (3).
FIG. 1G-I, shows that blood C-peptide levels were significantly reduced in human subjects treated with formulation (3)
Figure 1B:
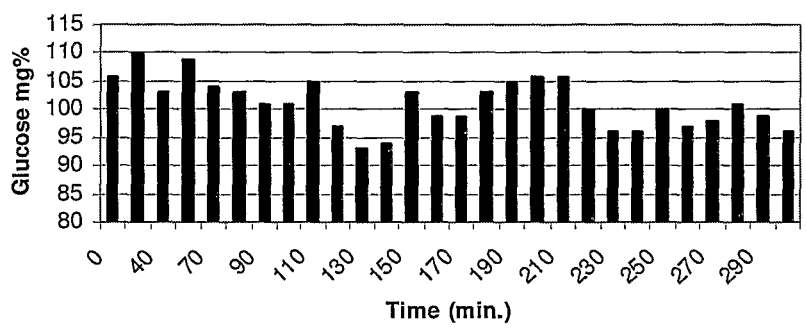
Figure 1C:
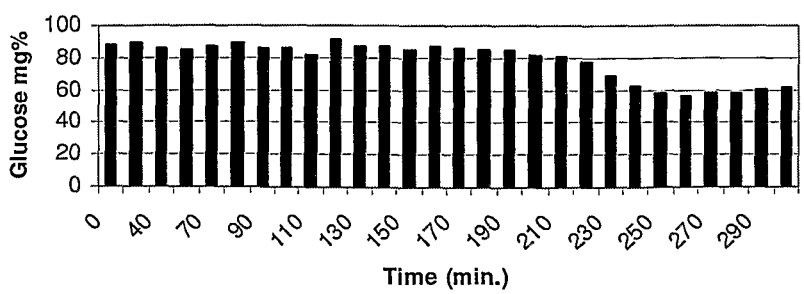

This invention provides compositions and methods comprising a protein and at least two protease inhibitors. In another, embodiment, the present invention provides compositions and methods comprising a protein and a first protease inhibitor and a second protease inhibitors. In another, embodiment, the present invention provides compositions and methods comprising a protein having a molecular weight of up to 100,000 Daltons and a first protease inhibitor and a second protease inhibitors.

In another, embodiment, the protein of the present invention has a molecular weight of 1,000-5,000 Daltons. In another, embodiment, the protein of the present invention has a molecular weight of 5,000-10,000 Daltons. In another, embodiment, the protein of the present invention has a molecular weight of 10,000-20,000 Daltons. In another, embodiment, the protein of the present invention has a molecular weight of 20,000-30,000 Daltons. In another, embodiment, the protein of the present invention has a molecular weight of 40,000-50,000 Daltons. In another, embodiment, the protein of the present invention has a molecular weight of 50,000-60,000 Daltons. In another, embodiment, the protein of the present invention has a molecular weight of 60,000-70,000 Daltons. In another, embodiment, the protein of the present invention has a molecular weight of 70,000-80,000 Daltons. In another, embodiment, the protein of the present invention has a molecular weight of 80,000-90,000 Daltons. In another, embodiment, the protein of the present invention has a molecular weight of 90,000-100,000 Daltons. In another, embodiment, the protein of the present invention has a molecular weight of 100,000-150,000 Daltons.

In another embodiment, the protein has a molecular weight (MW) of 1-50 kilodalton (kDa). In another embodiment, the MW is 1-45 kDa. In another embodiment, the MW is 1-40 kDa. In another embodiment, the MW is 1-35 kDa. In another embodiment, the MW is 1-30 kDa. In another embodiment, the MW is 1-25 kDa. In another embodiment, the MW is 1-20 kDa. In another embodiment, the MW is 10-50 kDa. In another embodiment, the MW is 15-50 kDa. In another embodiment, the MW is 20-50 kDa. In another embodiment, the MW is 25-50 kDa. In another embodiment, the MW is 30-50 kDa. In another embodiment, the MW is 35-50 kDa. In another embodiment, the MW is 1-100 kDa.

In another embodiment, the MW is 1-90 kDa. In another embodiment, the MW is 1-80 kDa. In another embodiment, the MW is 1-70 kDa. In another embodiment, the MW is 1-60 kDa. In another embodiment, the MW is 10-100 kDa. In another embodiment, the MW is 15-100 kDa. In another embodiment, the MW is 20-100 kDa. In another embodiment, the MW is 25-100 kDa. In another embodiment, the MW is 30-100 kDa. In another embodiment, the MW is 10-80 kDa. In another embodiment, the MW is 15-80 kDa. In another embodiment, the MW is 20-80 kDa. In another embodiment, the MW is 25-80 kDa. In another embodiment, the MW is 30-80 kDa. Each possibility represents a separate embodiment of the present invention.

In another embodiment, the MW is less than 20 kDa. In another embodiment, the MW is less than 25 kDa. In another embodiment, the MW is less than 30 kDa. In another embodiment, the MW is less than 35 kDa. In another embodiment, the MW is less than 40 kDa. In another embodiment, the MW is less than 45 kDa. In another embodiment, the MW is less than 50 kDa. In another embodiment, the MW is less than 55 kDa. In another embodiment, the MW is less than 60 kDa. In another embodiment, the MW is less than 65 kDa. In another embodiment, the MW is less than 70 kDa. In another embodiment, the MW is less than 75 kDa. In another embodiment, the MW is less than 80 kDa. In another embodiment, the MW is less than 85 kDa. In another embodiment, the MW is less than 90 kDa. In another embodiment, the MW is less than 95 kDa. In another embodiment, the MW is less than 100 kDa.

In another, embodiment, the protein of the present invention is insulin. In one embodiment, the insulin of methods and compositions of the present invention is human insulin. In another embodiment, the insulin is recombinant insulin. In another embodiment, the insulin is recombinant human insulin. In another embodiment, the insulin is bovine insulin. In another embodiment, the insulin is porcine insulin. In another embodiment, the insulin is whale insulin. In another embodiment, the insulin is a metal complex of insulin (e.g. a zinc complex of insulin, protamine zinc insulin, or globin zinc).

In another embodiment, the insulin is regular insulin. In another embodiment, the insulin is fast-acting insulin. In another embodiment, the insulin is lente insulin. In another embodiment, the insulin is semilente insulin. In another embodiment, the insulin is Ultralente insulin. In another embodiment, the insulin is NPH insulin. In another embodiment, the insulin is glargine insulin. In another embodiment, the insulin is lispro insulin. In another embodiment, the insulin is aspart insulin. In another embodiment, the insulin is a combination of two or more of any of the above types of insulin. In another embodiment, the insulin is any other type of insulin known in the art. Each possibility represents a separate embodiment of the present invention.

In one embodiment, the amount of insulin utilized in methods and compositions of the present invention is 0.5-3 units (u)/kg in humans. In one embodiment, the units used to measure insulin in methods and compositions of the present invention are USP Insulin Units. In one embodiment, the units used to measure insulin are milligrams. In another embodiment, one international Unit (IU) of Insulin is equivalent to 45.5 mg insulin.

In another embodiment, the amount of insulin is 0.1-1 u/kg. In another embodiment, the amount is 0.2-1 u/kg. In another embodiment, the amount is 0.3-1 u/kg. In another embodiment, the amount is 0.5-1 u/kg. In another embodiment, the amount is 0.1-2 u/kg. In another embodiment, the amount is 0.2-2 u/kg. In another embodiment, the amount is 0.3-2 u/kg. In another embodiment, the amount is 0.5-2 u/kg. In another embodiment, the amount is 0.7-2 u/kg. In another embodiment, the amount is 1-2 u/kg. In another embodiment, the amount is 1.2-2 u/kg. In another embodiment, the amount is 1-1.2 u/kg. In another embodiment, the amount is 1-1.5 u/kg. In another embodiment, the amount is 1-2.5 u/kg. In another embodiment, the amount is 1-3 u/kg. In another embodiment, the amount is 2-3 u/kg. In another embodiment, the amount is 1-5 u/kg. In another embodiment, the amount is 2-5 u/kg. In another embodiment, the amount is 3-5 u/kg.

In another embodiment, the amount of insulin is 0.1 u/kg. In another embodiment, the amount is 0.2 u/kg. In another embodiment, the amount is 0.3 u/kg. In another embodiment, the amount is 0.4 u/kg. In another embodiment, the amount is 0.5 u/kg. In another embodiment, the amount is 0.6 u/kg. In another embodiment, the amount is 0.8 u/kg. In another embodiment, the amount is 1 u/kg. In another embodiment, the amount is 1.2 u/kg. In another embodiment, the amount is 1.4 u/kg. In another embodiment, the amount is 1.6 u/kg. In another embodiment, the amount is 1.8 u/kg. In another embodiment, the amount is 2 u/kg. In another embodiment, the amount is 2.2 u/kg. In another embodiment, the amount is 2.5 u/kg. In another embodiment, the amount is 3 u/kg.

In another embodiment, the amount of insulin is 1-10 u. In another embodiment, the amount is 2-10 u. In another embodiment, the amount is 3-10 u. In another embodiment, the amount is 5-10 u. In another embodiment, the amount is 1-20 u. In another embodiment, the amount is 2-20 u. In another embodiment, the amount is 3-20 u. In another embodiment, the amount is 5-20 u. In another embodiment, the amount is 7-20 u. In another embodiment, the amount is 10-20 u. In another embodiment, the amount is 12-20 u. In another embodiment, the amount is 10-12 u. In another embodiment, the amount is 10-15 u. In another embodiment, the amount is 10-25 u. In another embodiment, the amount is 10-30 u. In another embodiment, the amount is 20-30 u. In another embodiment, the amount is 10-50 u. In another embodiment, the amount is 20-50 u. In another embodiment, the amount is 30-50 u. In another embodiment, the amount is 20-100 u. In another embodiment, the amount is 30-100 u. In another embodiment, the amount is 100-150 u. In another embodiment, the amount is 100-250 u. In another embodiment, the amount is 100-300 u. In another embodiment, the amount is 200-300 u. In another embodiment, the amount is 100-500 u. In another embodiment, the amount is 200-500 u. In another embodiment, the amount is 300-500 u. In another embodiment, the amount is 200-1000 u. In another embodiment, the amount is 300-1000 u.

In another embodiment, the amount of insulin is 1 u. In another embodiment, the amount is 2 u. In another embodiment, the amount is 3 u. In another embodiment, the amount is 4 u. In another embodiment, the amount is 5 u. In another embodiment, the amount is 6 u. In another embodiment, the amount is 8 u. In another embodiment, the amount is 10 u. In another embodiment, the amount is 12 u. In another embodiment, the amount is 14 u. In another embodiment, the amount is 16 u. In another embodiment, the amount is 18 u. In another embodiment, the amount is 20 u. In another embodiment, the amount is 22 u. In another embodiment, the amount is 25 u. In another embodiment, the amount is 30 u. In another embodiment, the amount is 50 u. In another embodiment, the amount is 80 u. In another embodiment, the amount is 100 u. In another embodiment, the amount is 120 u. In another embodiment, the amount is 140 u. In another embodiment, the amount is 160 u. In another embodiment, the amount is 180 u. In another embodiment, the amount is 200 u. In another embodiment, the amount is 300 u. In another embodiment, the amount is 500 u.

In another embodiment, the protein is Exenatide. In another embodiment, the oral formulations of the present invention protect Exenatide breakdown in the stomach. In another embodiment, Exenatide formulation of the invention controls blood sugar levels. In another embodiment, Exenatide formulation of the invention helps control blood sugar levels. In another embodiment, Exenatide formulation of the invention induces pancreatic production of insulin. In another embodiment, Exenatide formulation of the invention is used to treat type 2 (non-insulin dependent) diabetes. In another embodiment, Exenatide formulation of the invention is used in conjunction with other diabetes medicines.

In another embodiment, the amount of Exenatide in a formulation as described herein is 10 mcg to 1 mg. In another embodiment, the amount of Exenatide in a formulation as described herein is 10 mcg to 25 mcg. In another embodiment, the amount of Exenatide in a formulation as described herein is 25 mcg to 50 mcg. In another embodiment, the amount of Exenatide in a formulation as described herein is 50 meg to 60 mcg. In another embodiment, the amount of Exenatide in a formulation as described herein is 60 mcg to 70 mcg. In another embodiment, the amount of Exenatide in a formulation as described herein is 70 mcg to 80 mcg. In another embodiment, the amount of Exenatide in a formulation as described herein is 80 mcg to 90 mcg. In another embodiment, the amount of Exenatide in a formulation as described herein is 90 mcg to 100 mcg. In another embodiment, the amount of Exenatide in a formulation as described herein is 100 mcg to 110 mcg. In another embodiment, the amount of Exenatide in a formulation as described herein is 110 mcg to 125 mcg. In another embodiment, the amount of Exenatide in a formulation as described herein is 125 mcg to 150 mcg. In another embodiment, the amount of Exenatide in a formulation as described herein is 150 mcg to 175 mcg. In another embodiment, the amount of Exenatide in a formulation as described herein is 175 mcg to 200 mcg. In another embodiment, the amount of Exenatide in a formulation as described herein is 200 mcg to 220 mcg. In another embodiment, the amount of Exenatide in a formulation as described herein is 220 mcg to 240 mcg. In another embodiment, the amount of Exenatide in a formulation as described herein is 240 meg to 260 mcg. In another embodiment, the amount of Exenatide in a formulation as described herein is 260 meg to 300 mcg.

In another embodiment, the amount of Exenatide in a formulation as described herein is 300 mcg to 350 mcg. In another embodiment, the amount of Exenatide in a formulation as described herein is 350 mcg to 400 mcg. In another embodiment, the amount of Exenatide in a formulation as described herein is 400 mcg to 450 mcg. In another embodiment, the amount of Exenatide in a formulation as described herein is 450 mcg to 500 mcg. In another embodiment, the amount of Exenatide in a formulation as described herein is 550 meg to 600 mcg. In another embodiment, the amount of Exenatide in a formulation as described herein is 600 mcg to 700 mcg. In another embodiment, the amount of Exenatide in a formulation as described herein is 700 meg to 800 mcg. In another embodiment, the amount of Exenatide in a formulation as described herein is 800 mcg to 900 mcg. In another embodiment, the amount of Exenatide in a formulation as described herein is 900 mcg to 1 mg.

In another embodiment, the Exenatide formulation as described herein is taken once a day. In another embodiment, the Exenatide formulation as described herein is taken twice a day. In another embodiment, the Exenatide formulation as described herein is taken three times a day. In another embodiment, the Exenatide formulation as described herein is taken four times a day. In another embodiment, the Exenatide formulation as described herein is taken five times a day. In another embodiment, one of skill in the art determines the dosage of a Exenatide formulation as described herein. In another embodiment, one of skill in the art determines the daily dose of a Exenatide formulation as described herein. In another embodiment, one of skill in the art determines the daily dosing regimen of a Exenatide formulation as described herein.

In another embodiment, the Exenatide formulation as described herein is taken at least 15 minutes before a meal. In another embodiment, the Exenatide formulation as described herein is taken at least 30 minutes before a meal. In another embodiment, the Exenatide formulation as described herein is taken at least 45 minutes before a meal. In another embodiment, the Exenatide formulation as described herein is taken at least 60 minutes before a meal. In another embodiment, the Exenatide formulation as described herein is taken at least 75 minutes before a meal. In another embodiment, the Exenatide formulation as described herein is taken at least 90 minutes before a meal. In another embodiment, the Exenatide formulation as described herein is taken at least 100 minutes before a meal. In another embodiment, the Exenatide formulation as described herein is taken at least 120 minutes before a meal. In another embodiment, the Exenatide formulation as described herein is taken at least 150 minutes before a meal. In another embodiment, the Exenatide formulation as described herein is taken at least 180 minutes before a meal.

In another embodiment, the Exenatide formulation as described herein reduces the side effects associated with an injectable dosage form comprising Exenatide. In another embodiment, the Exenatide formulation as described herein reduces nausea as a side effect which is associated with an injectable dosage form comprising Exenatide. In another embodiment, the Exenatide formulation as described herein does not induce nausea as a side effect which is associated with an injectable dosage form comprising Exenatide.

As provided herein, protease inhibitors protect the protein of the present invention from cleavage. In another embodiment, the present invention provides that protease inhibitors protect insulin of the present invention from cleavage. In another, embodiment, the present invention provides that protease inhibitors facilitate the protein absorption in the intestine of a subject. In another, embodiment, the present invention provides that protease inhibitors facilitate the absorption of insulin in the intestine of a subject.

In another embodiment, the present invention provides the use of more than two protease inhibitors in a single composition or a method. In another, embodiment, the present invention provides that the first and the second protease inhibitors are serpins. In another, embodiment, the present invention provides that serpins are trypsin inhibitors. In another, embodiment, the present invention provides that the first and the second protease inhibitors are serpins such as but not limited to: Alpha 1-antitrypsin, Antitrypsin-related protein, Alpha 1-antichymotrypsin, Kallistatin, Protein C inhibitor, Cortisol binding globulin, Thyroxine-binding globulin, Angiotensinogen, Centerin, Protein Z-related protease inhibitor, Vaspin, Monocyte neutrophil elastase inhibitor, Plasminogen activator inhibitor-2, Squamous cell carcinoma antigen-1 (SCCA-1), Squamous cell carcinoma antigen-2 (SCCA-2), Maspin, PI-6, Megsin, PI-8, PI-9, Bomapin, Yukopin, Hurpin/Headpin, Antithrombin, Heparin cofactor II, Plasminogen activator inhibitor 1, Glia derived nexin/Protease nexin I, Pigment epithelium derived factor, Alpha 2-antiplasmin, Complement 1-inhibitor, 47 kDa Heat shock protein (HSP47), Neuroserpin, or Pancpin.

In another embodiment, the present invention provides that the first and the second protease inhibitors are trypsin inhibitors such as but not limited to: Lima bean trypsin inhibitor, Aprotinin, soy bean trypsin inhibitor (SBTI), or Ovomucoid. In another, embodiment, the present invention provides that the first and the second protease inhibitors are Lima bean trypsin inhibitor and Aprotinin. In another, embodiment, the present invention provides that the first and the second protease inhibitors are Lima bean trypsin inhibitor and soy bean trypsin inhibitor (SBTI). In another, embodiment, the present invention provides that the first and the second protease inhibitors are Lima bean trypsin inhibitor, and Ovomucoid. In another, embodiment, the present invention provides that the first and the second protease inhibitors are Aprotinin and soy bean trypsin inhibitor (SBTI). In another, embodiment, the present invention provides that the first and the second protease inhibitors are Aprotinin and Ovomucoid. In another, embodiment, the present invention provides that the first and the second protease inhibitors are soy bean trypsin inhibitor (SBTI) and Ovomucoid. In another, embodiment, the present invention provides that the first protease inhibitor is kunitz. In another, embodiment, the present invention provides that the second protease inhibitor is kunitz. In another, embodiment, the present invention provides that the first protease inhibitor is Bowman-Birk protease inhibitor (BBI). In another, embodiment, the present invention provides that the second protease inhibitor is Bowman-Birk protease inhibitor (BBI).

In another embodiment, the present invention provides that the first protease inhibitor is a serpine and the second protease inhibitor is a Cysteine protease inhibitor. In another, embodiment, the present invention provides that Cysteine protease inhibitors of the invention comprise: cystatin, type 1 cystatins (or stefins), Cystatins of type 2, human cystatins C, D, S, SN, and SA, cystatin E/M, cystatin F, type 3 cystatins, or kininogens.

In another embodiment, the present invention provides that the first protease inhibitor is a serpine and the second protease inhibitor is a Threonine protease inhibitor. In another, embodiment, the present invention provides that Threonine protease inhibitors of the invention comprise: Bortezomib, MLN-519, ER-807446, TMC-95A.

In another embodiment, the present invention provides that the first protease inhibitor is a serpine and the second protease inhibitor is an Aspartic protease inhibitor. In another, embodiment, the present invention provides that Aspartic protease inhibitors of the invention comprise: $\alpha_2$-Macroglobulin, Pepstatin A, Aspartic protease inhibitor 11, Aspartic protease inhibitor 1, Aspartic protease inhibitor 2, Aspartic protease inhibitor 3, Aspartic protease inhibitor 4, Aspartic protease inhibitor 5, Aspartic protease inhibitor 6, Aspartic protease inhibitor 7, Aspartic protease inhibitor 8, Aspartic protease inhibitor 9, Pepsin inhibitor Dit33, Aspartyl protease inhibitor, or Protease A inhibitor 3.

In another embodiment, the present invention provides that the first protease inhibitor is a serpine and the second protease inhibitor is a Metalloprotease inhibitor. In another, embodiment, the present invention provides that Metalloprotease inhibitors of the invention comprise: Angiotensin-1-converting enzyme inhibitory peptide, Antihemorragic factor BJ46a, Beta-casein, Proteinase inhibitor CeKI, Venom metalloproteinase inhibitor DM43, Carboxypeptidase A inhibitor, smpI, IMPI, Alkaline proteinase, inh, Latexin, Carboxypeptidase inhibitor, Antihemorragic factor HSF, Testican-3, SPOCK3, TIMP1, Metalloproteinase inhibitor 1, Metalloproteinase inhibitor 2, TIMP2, Metalloproteinase inhibitor 3, TIMP3, Metalloproteinase inhibitor 4, TIMP4, Putative metalloproteinase inhibitor tag-225, Tissue inhibitor of metalloprotease, WAP, kazal, immunoglobulin, or kunitz and NTR domain-containing protein 1.

In another embodiment, the present invention provides that the first protease inhibitor is a Cysteine protease inhibitor and the second protease inhibitor is a Metalloprotease inhibitor. In another embodiment, the present invention provides that the first protease inhibitor is a Cysteine protease inhibitor and the second protease inhibitor is a Trypsin inhibitor. In another embodiment, the present invention provides that the first protease inhibitor is a Cysteine protease inhibitor and the second protease inhibitor is a Threonine protease inhibitor. In another embodiment, the present invention provides that the first protease inhibitor is a Cysteine protease inhibitor and the second protease inhibitor is an Aspartic protease inhibitor. In another embodiment, the present invention provides that the first protease inhibitor is a Cysteine protease inhibitor and the second protease inhibitor is a Metalloprotease inhibitor. In another embodiment, the present invention provides that the first protease inhibitor is a Trypsin inhibitor and the second protease inhibitor is a Metalloprotease inhibitor. In another embodiment, the present invention provides that the first protease inhibitor is a Trypsin inhibitor and the second protease inhibitor is a Threonine protease inhibitor. In another embodiment, the present invention provides that the first protease inhibitor is a Trypsin inhibitor and the second protease inhibitor is an Aspartic protease inhibitor. In another embodiment, the present invention provides that the first protease inhibitor is a Trypsin inhibitor and the second protease inhibitor is a Metalloprotease inhibitor. In another embodiment, the present invention provides that the first protease inhibitor is an Aspartic protease inhibitor and the second protease inhibitor is a Metalloprotease inhibitor. In another embodiment, the present invention provides that the first protease inhibitor is an Aspartic protease inhibitor and the second protease inhibitor is a Threonine protease inhibitor. In another embodiment, the present invention provides that the first protease inhibitor is an Aspartic protease inhibitor and the second protease inhibitor is a Metalloprotease inhibitor.

In another embodiment, the present invention provides that the first protease inhibitor is a Cysteine protease inhibitor. In another embodiment, the present invention provides that the first protease inhibitor is a Metalloprotease inhibitor. In another embodiment, the present invention provides that the first protease inhibitor is a Trypsin inhibitor. In another embodiment, the present invention provides that the first protease inhibitor is a Threonine protease inhibitor. In another embodiment, the present invention provides that the first protease inhibitor is an Aspartic protease inhibitor. In another embodiment, the present invention provides that the first protease inhibitor is a Metalloprotease inhibitor. In another embodiment, the present invention provides that the second protease inhibitor is a Trypsin inhibitor. In another embodiment, the present invention provides that the second protease inhibitor is a Metalloprotease inhibitor. In another embodiment, the present invention provides that the second protease inhibitor is a Threonine protease inhibitor. In another embodiment, the present invention provides that the second protease inhibitor is an Aspartic protease inhibitor.

In some embodiments, protease inhibitors comprise suicide inhibitor, transition state inhibitor, or chelating agents.

In some embodiments, the first and second protease inhibitors of the present invention comprise any combination of two different protease inhibitors such as but not limited to: AEBSF-HCl, (epsilon)-aminocaproic acid, (alpha) 1-antichymotypsin, antipain, antithrombin III, (alpha) 1-antitrypsin ([alpha] 1-proteinase inhibitor), APMSF-HCl (4-amidinophenyl-methane sulfonyl-fluoride), sprotinin, benzamidine-HCl, chymostatin, DFP (diisopropylfluorophosphate), leupeptin, PEFABLOC® SC (4-(2-Aminoethyl)-benzenesulfonyl fluoride hydrochloride), PMSF (phenylmethyl sulfonyl fluoride), TLCK (1-Chloro-3-tosylamido-7-amino-2-heptanone HCl), TPCK (1-Chloro-3-tosylamido-4-phenyl-2-butanone), Ovomucoid, trypsin inhibitor from soybean, Aprotinin, pentamidine isethionate, pepstatin, guanidium, alpha2-macroglobulin, a chelating agent of zinc, iodoacetate, zinc. Each possibility represents a separate embodiment of the present invention.

In another embodiment, a formulation comprising a combination of protease inhibitors as described comprise Aprotinin and BBI. In another embodiment, a formulation comprising a combination of protease inhibitors as described comprise Aprotinin and Kunitz. In another embodiment, a formulation comprising a combination of protease inhibitors as described comprise BBI and Kunitz. In another embodiment, a formulation comprising a combination of protease inhibitors as described comprise SBTI and BBI. In another embodiment, a formulation comprising a combination of protease inhibitors as described comprise kunitz and SBTI.

In another embodiment, the amount of a first or a second protease inhibitor utilized in methods and compositions of the present invention is 0.1 mg/dosage unit. In another embodiment, the amount of protease inhibitor is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of a first or a second protease inhibitor is 0.1-1 mg/dosage unit. In another embodiment, the amount of protease inhibitor is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit.

In another embodiment, the amount of a first or a second protease inhibitor utilized in methods and compositions of the present invention is 1000 k.i.u. (kallikrein inactivator units)/pill. In another embodiment, the amount is 10 k.i.u./dosage unit. In another embodiment, the amount is 12 k.i.u./dosage unit. In another embodiment, the amount is 15 k.i.u./dosage unit. In another embodiment, the amount is 20 k.i.u./dosage unit. In another embodiment, the amount is 30 k.i.u./dosage unit. In another embodiment, the amount is 40 k.i.u./dosage unit. In another embodiment, the amount is 50 k.i.u./dosage unit. In another embodiment, the amount is 70 k.i.u./dosage unit. In another embodiment, the amount is 100 k.i.u./dosage unit. In another embodiment, the amount is 150 k.i.u./dosage unit. In another embodiment, the amount is 200 k.i.u./dosage unit. In another embodiment, the amount is 300 k.i.u./dosage unit. In another embodiment, the amount is 500 k.i.u./dosage unit. In another embodiment, the amount is 700 k.i.u./dosage unit. In another embodiment, the amount is 1500 k.i.u./dosage unit. In another embodiment, the amount is 3000 k.i.u./dosage unit. In another embodiment, the amount is 4000 k.i.u./dosage unit. In another embodiment, the amount is 5000 k.i.u./dosage unit. Each amount of a first or a second protease inhibitor represents a separate embodiment of the present invention.

In some embodiments, omega-3 fatty acid can be found in vegetable sources such as the seeds of chia, perilla, flax, walnuts, purslane, lingonberry, seabuckthorn, and hemp. In some embodiments, omega-3 fatty acids can also be found in the fruit of the acai palm. In another embodiment, the omega-3 fatty acid has been provided in the form of a synthetic omega-3 fatty acid. In one embodiment, the omega-3 fatty acid of methods and compositions of the present invention has been provided to the composition in the form of a fish oil. In another embodiment, the omega-3 fatty acid has been provided in the form of canola oil. In another embodiment, the omega-3 fatty acid has been provided in the form of flaxseed oil. In another embodiment, the omega-3 fatty acid has been provided in the form of any other omega-3 fatty acid-rich source known in the art. In another embodiment, the omega-3 fatty acid has been provided in the form of a synthetic omega-3 fatty acid. Each form of omega-3 fatty acids represents a separate embodiment of the present invention.

In another embodiment, the omega-3 fatty acid of methods and compositions of the present invention is an omega-3 polyunsaturated fatty acid. In another embodiment, the omega-3 fatty acid is DHA, an omega-3, polyunsaturated, 22-carbon fatty acid also referred to as 4, 7, 10, 13, 16, 19-docosahexaenoic acid. In another embodiment, the omega-3 fatty acid is □-linolenic acid (9, 12, 15-octadecatrienoic acid). In another embodiment, the omega-3 fatty acid is stearidonic acid (6, 9, 12, 15-octadecatetraenoic acid). In another embodiment, the omega-3 fatty acid is eicosatrienoic acid (ETA; 11, 14, 17-eicosatrienoic acid). In another embodiment, the omega-3 fatty acid is eicosatetraenoic acid (8, 11, 14, 17-eicosatetraenoic acid). In one embodiment, the omega-3 fatty acid is eicosapentaenoic acid (EPA; 5, 8, 11, 14, 17-eicosapentaenoic acid). In another embodiment, the omega-3 fatty acid is eicosahexaenoic acid (also referred to as "EPA"; 5, 7, 9, 11, 14, 17-eicosahexaenoic acid). In another embodiment, the omega-3 fatty acid is docosapentaenoic acid (DPA; 7, 10, 13, 16, 19-docosapenatenoic acid). In another embodiment, the omega-3 fatty acid is tetracosahexaenoic acid (6, 9, 12, 15, 18, 21-tetracosahexaenoic acid). In another embodiment, the omega-3 fatty acid is any other omega-3 fatty acid known in the art. Each omega-3 fatty acid represents a separate embodiment of the present invention.

In another embodiment, compositions of the present invention further comprise a substance that enhances absorption of a protein of the invention through an intestinal mucosal barrier. In another embodiment, compositions of the present invention further comprise a substance that enhances absorption of insulin through an intestinal mucosal barrier. In another embodiment, compositions of the present invention further comprise a substance that enhances absorption of Exenatide through an intestinal mucosal barrier. In another embodiment, compositions of the present invention further comprise a substance that reduces the degradation of Exenatide in the digestive system. In another embodiment, compositions of the present invention further comprise a substance that reduces the degradation of Exenatide in the stomach. In another embodiment, compositions of the present invention further comprise a substance that reduces the degradation of Exenatide in the intestine. Such a substance is referred to herein as an "enhancer." As provided herein, enhancers, when used together with omega-3 fatty acids or protease inhibitors, enhance the ability of a protein to be absorbed in the intestine. As provided herein, enhancers, when used together with omega-3 fatty acids and/or protease inhibitors, enhance the ability of insulin to be absorbed in the intestine. As provided herein, enhancers, when used together with omega-3 fatty acids and/or protease inhibitors, enhance the ability of Exenatide to be absorbed in the intestine.

In one embodiment, the enhancer is didecanoylphosphatidylcholine (DDPC). In one embodiment, the enhancer is a chelating agent such as ethylenediaminetetraacetic acid (EDTA) or egtazic acid EGTA. In another embodiment, EDTA is sodium-EDTA. In some embodiments, the enhancer is NO donor. In some embodiments, the enhancer is a bile acid, glycine-conjugated form of a bile acid, or an alkali metal salt. In one embodiment, absorption enhancement is achieved through utilization of a combination of α-galactosidase and β-mannanase. In some embodiments, the enhancer is a fatty acid such as sodium caprate. In one embodiment, the enhancer is sodium glycocholate. In one embodiment, the enhancer is sodium salicylate. In one embodiment, the enhancer is n-dodecyl-β-D-maltopyranoside. In some embodiments, surfactants serve as absorption enhancer. In one embodiment, the enhancer is chitisan such as N,N,N-trimethyl chitosan chloride (TMC).

In one embodiment, NO donors of the present invention comprise 3-(2-Hydroxy-1-(1-methylethyl)-2-nitrosohydrazino)-1-propanamine, N-ethyl-2-(1-ethyl-hydroxy-2-nitrosohydrazino)-ethanamine, or S-Nitroso-N-acetylpenicillamine In another embodiment, the bile acid is cholic acid. In another embodiment, the bile acid is chenodeoxycholic acid. In another embodiment, the bile acid is taurocholic acid. In another embodiment, the bile acid is taurochenodeoxycholic acid. In another embodiment, the bile acid is glycocholic acid. In another embodiment, the bile acid is glycochenocholic acid. In another embodiment, the bile acid is 3 beta-monohydroxychloric acid. In another embodiment, the bile acid is lithocholic acid. In another embodiment, the bile acid is 5 beta-cholanic acid. In another embodiment, the bile acid is 3,12-diol-7-one-5 beta-cholanic acid. In another embodiment, the bile acid is 3 alpha-hydroxy-12-ketocholic acid. In another embodiment, the bile acid is 3 beta-hydroxy-12-ketocholic acid. In another embodiment, the bile acid is 12 alpha-3 beta-dihydrocholic acid. In another embodiment, the bile acid is ursodesoxycholic acid.

In one embodiment, the enhancer is a nonionic surfactant. In one embodiment, the enhancer is a nonionic polyoxyethylene ether surface active agent (e.g one having an HLB value of 6 to 19, wherein the average number of polyoxyethylene units is 4 to 30). In another embodiment, the enhancer is an anionic surface active agents. In another embodiment, the enhancer is a cationic surface active agent. In another embodiment, the enhancer is an ampholytic surface active agent. In one embodiment, zwitteruionic surfactants such as acylcarnitines serve as absorption enhancers.

In another embodiment, the amount of enhancer utilized in methods and compositions of the present invention is 0.1 mg/dosage unit. In another embodiment, the amount of enhancer is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of enhancer is 0.1-1 mg/dosage unit. In another embodiment, the amount of enhancer is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit. Each type and amount of enhancer represents a separate embodiment of the present invention.

In another embodiment, compositions of the present invention further comprise a coating that inhibits digestion of the composition in the stomach of a subject. In one embodiment, coating inhibits digestion of the composition in the stomach of a subject. In one embodiment, the coated dosage forms of the present invention release drug when pH move towards alkaline range. In one embodiment, coating is a monolayer, wherein in other embodiments coating applied in multilayers. In one embodiment, coating is a bioadhesive polymer that selectively binds the intestinal mucosa and thus enables drug release in the attachment site. In one embodiment, the enteric coating is an enteric film coating. In some embodiment, coating comprises biodegradable polysaccharide, chitosan, aquateric aqueous, aquacoat ECD, azo polymer, cellulose acetate phthalate, cellulose acetate trimelliate, hydroxypropylmethyl cellulose phthalate, gelatin, poly vinyl acetate phthalate, hydrogel, pulsincap, or a combination thereof. In one embodiment, pH sensitive coating will be used according to the desired release site and/or profile as known to one skilled in the art.

In one embodiment, the coating is an enteric coating. Methods for enteric coating are well known in the art, and are described, for example, in Siepmann F, Siepmann J et al, Blends of aqueous polymer dispersions used for pellet coating: importance of the particle size. J Control Release 2005; 105 (3): 226-39; and Huyghebaert N, Vermeire A, Remon J P. In vitro evaluation of coating polymers for enteric coating and human ileal targeting. Int J Pharm 2005; 298 (1): 26-37. Each method represents a separate embodiment of the present invention.

In another embodiment, Eudragit®, an acrylic polymer, is used as the enteric coating. The use of acrylic polymers for the coating of pharmaceutical preparations is well known in the art. Eudragit Acrylic Polymers have been shown to be safe, and are neither absorbed nor metabolized by the body, but rather are eliminated.

In another embodiment, the coating is a gelatin coating. In another embodiment, microencapsulation is used to protect the insulin against decomposition in the stomach. In another embodiment, the coating is a gelatin coating. In another embodiment, microencapsulation is used to protect Exenatide against decomposition in the stomach. Methods for applying a gelatin coating and for microencapsulation are well known in the art. Each method represents a separate embodiment of the present invention.

In another embodiment, the coating is a film-coating. In another embodiment, the coating is ethylcellulose. In another embodiment, the coating is a water-based dispersion of ethylcellulose, e.g. hydroxypropylmethylcelullose (HPMC) E15. In another embodiment, the coating is a gastro-resistant coatings, e.g. a polymer containing carboxylic acid groups as a functional moiety. In another embodiment, the coating is a monolithic matrix. In another embodiment, the coating is a cellulose ether (e.g. hypromellose (HPMC). Each type of coating represents a separate embodiment of the present invention.

In one embodiment, the protein is a recombinant protein. In one embodiment, the protein is an insulin. In another embodiment, the protein is a glucagon. In another embodiment, the protein is an interferon gamma. In another embodiment, the protein is an interferon alpha. In another embodiment, the protein is a growth hormone. In another embodiment, the protein is an erythropoietin. In another embodiment, the protein is Exenatide. In another embodiment, the protein is granulocyte colony stimulating factor (G-CSF). In another embodiment, the protein is any other protein known in the art.

In another embodiment, the protein is a growth hormone. In one embodiment, the growth hormone is somatotropin. In another embodiment, the growth hormone is Insulin Growth Factor-I (IGF-I). In another embodiment, the growth hormone is any other growth hormone known in the art.

The molecular weights of some of the proteins mentioned above are as follows: insulin—6 kilodalton (kDa); glucagon—3.5 kDa; interferon, 28 kDa, growth hormone—21.5-47 kDa; human serum albumin—69 kDa; erythropoietin—34 kDa; G-CSF—30-34 kDa. Thus, in one embodiment, the molecular weight of these proteins is appropriate for administration by methods of the present invention.

In another embodiment, methods and compositions of the present invention are used to administer a human serum albumin. Human serum albumin is not, in one embodiment, considered to be a pharmaceutically-active component; however, it can be used in the context of the present invention as a therapeutically-beneficial carrier for an active component. Each type of protein represents a separate embodiment of the present invention.

In one embodiment, the protein is an enzyme. In some embodiments, the protein is a receptor ligand, transporter, or a storage protein. In one embodiment, the protein is a structural protein.

In some embodiments, the enzyme is an oxidoreductase, transferase, hydrolase, lyase, isomerase, or ligase. In some embodiments, oxidoreductases act on the aldehyde or oxo group of donors, on the CH—CH group of donors, on the CH—NH(2) group of donors, on the CH—NH group of donors, on NADH or NADPH, on the CH—OH group of donors, on nitrogenous compounds as donors, on a sulfur group of donors, on a heme group of donors, on diphenols and related substances as donors, on a peroxide as acceptor, on hydrogen as donor, on single donors with incorporation of molecular oxygen, on paired donors, on superoxide as acceptor, oxidizing metal ions, on CH or CH(2) groups, on iron-sulfur proteins as donors, on reduced flavodoxin as donor, on phosphorus or arsenic in donors, or on x-H and y-H to form an x-y bond.

In some embodiments, transferases are acyltransferases or glycosyltransferases. In some embodiments, transferases transfer aldehyde or ketone residues. In some embodiments, transferases transfer alkyl or aryl groups, other than methyl groups. In some embodiments, transferases transfer nitrogenous, phosphorous, sulfur or selenium containing groups.

In some embodiments, hydrolases are glycosylases or act on ether bonds, on peptide bonds, on carbon-nitrogen bonds, other than peptide bonds, on acid anhydrides, on carbon-carbon bonds, on halide bonds, on phosphorus-nitrogen bonds, on sulfur-nitrogen bonds, on carbon-phosphorus bonds, on sulfur-sulfur bonds, or on carbon-sulfur bonds.

In some embodiments, lyases are carbon-carbon lyases, carbon-oxygen lyases, carbon-nitrogen lyases, carbon-sulfur lyases, carbon-halide lyases, phosphorus-oxygen lyases, or other lyases.

In some embodiments, isomerases are racemases or epimerases, cis-trans-isomerases, intramolecular oxidoreductases, intramolecular transferases, intramolecular lyases, or other isomerases.

In some embodiments, ligases form carbon-sulfur bonds, carbon-nitrogen bonds, carbon-carbon bonds, phosphoric ester bonds, or nitrogen-metal bonds.

In some embodiments, transporter proteins are annexins, ATP-binding cassette transporters, hemoglobin, ATPases, calcium channels, potassium channels, sodium channels, or solute carriers.

In some embodiments, storage proteins comprise albumins, lactoglobulins, casein ovomucin, ferritin, phosvitin, lactoferrin, or vitellogenin. In one embodiment, albumins comprise avidin, ovalbumin, serum albumin, parvalbumin, c-reactive protein prealbumin, conalbumin, ricin, lactalbumin, methemalbumin, or transthyretin.

In some embodiments, structural proteins comprise amyloid, collagen elastin, or fibrillin.

In some embodiments, the protein is a viral protein, bacterial protein, invertebrate protein, or vertebrate protein. In some embodiments, the protein is a recombinant protein. In one embodiment, the protein is a recombinant protein. In one embodiment, the recombinant protein is a recombinant human protein.

In one embodiment, the present invention provides a composition comprising an insulin protein and at least two protease inhibitors. In one embodiment, the present invention provides a composition comprising a Exenatide and at least two protease inhibitors. In one embodiment, the present invention provides a composition comprising an insulin protein and two protease inhibitors. In one embodiment, the present invention provides a composition comprising a Exenatide and two protease inhibitors. In one embodiment, the present invention provides a composition comprising a Exenatide and 3 protease inhibitors. In one embodiment, the present invention provides a composition comprising an insulin protein and 4 protease inhibitors. In one embodiment, the present invention provides a composition comprising a Exenatide and 4 protease inhibitors. In one embodiment, the present invention provides a composition comprising an insulin protein and 5 protease inhibitors. In one embodiment, the present invention provides a composition comprising a Exenatide and 5 protease inhibitors. In one embodiment, the present invention provides a composition comprising an insulin protein and at least 5 protease inhibitors. In one embodiment, the present invention provides a composition comprising an insulin protein and at least 7 protease inhibitors. In one embodiment, the present invention provides a composition comprising an insulin protein and at least 10 protease inhibitors.

In another embodiment, the present invention provides a composition comprising an active protein of the invention, at least two protease inhibitors, and an omega-3 fatty acid. In another embodiment, the present invention provides a composition comprising an active protein of the invention, at least two protease inhibitors, EDTA or a salt thereof (such as Na-EDTA), and an omega-3 fatty acid.

In another embodiment, the present invention provides that the use of two protease inhibitors in a single oral composition dramatically, unexpectedly, increase the bioavailability of a protein of the invention. In another embodiment, the present invention provides that the use of two protease inhibitors in a single oral composition dramatically, unexpectedly, increase the bioavailability of insulin. In another embodiment, the present invention provides that the use of two protease inhibitors in a single oral composition dramatically, unexpectedly, increase the bioavailability of Exenatide. In another embodiment, the present invention provides that the use of two serpins in a single oral composition dramatically, unexpectedly, increase the bioavailability of a protein of the invention. In another embodiment, the present invention provides that the use of two serpins in a single oral composition dramatically, unexpectedly, increase the bioavailability of insulin. In another embodiment, the present invention provides that the use of two serpins in a single oral composition dramatically, unexpectedly, increase the bioavailability of Exenatide. In another embodiment, the present invention provides that the use of two trypsin inhibitors in a single oral composition dramatically, unexpectedly, increase the bioavailability of a protein of the invention. In another embodiment, the present invention provides that the use of two trypsin inhibitors in a single oral composition dramatically, unexpectedly, increase the bioavailability of insulin. In another embodiment, the present invention provides that the use of two trypsin inhibitors in a single oral composition dramatically, unexpectedly, increase the bioavailability of Exenatide. In another embodiment, the present invention provides that the use of SBTI and Aprotinin in a single oral composition dramatically, unexpectedly, increase the bioavailability of a protein of the invention. In another embodiment, the present invention provides that the use of SBTI and Aprotinin in a single oral composition dramatically, unexpectedly, increase the bioavailability of insulin. In another embodiment, the present invention provides that the use of SBTI and Aprotinin in a single oral composition dramatically, unexpectedly, increase the bioavailability of Exenatide.

In another embodiment, the present invention provides that the use of a serpin and a Cysteine protease inhibitor in a single oral composition dramatically, unexpectedly, increase the bioavailability of a protein of the invention. In another embodiment, the present invention provides that the use of a serpin and a Cysteine protease inhibitor in a single oral composition dramatically, unexpectedly, increase the bioavailability of insulin. In another embodiment, the present invention provides that the use of a serpin and a Cysteine protease inhibitor in a single oral composition dramatically, unexpectedly, increase the bioavailability of Exenatide. In another embodiment, the present invention provides that the use of a serpin and a Threonine protease inhibitor in a single oral composition dramatically, unexpectedly, increase the bioavailability of a protein of the invention. In another embodiment, the present invention provides that the use of a serpin and a Threonine protease inhibitor in a single oral composition dramatically, unexpectedly, increase the bioavailability of insulin. In another embodiment, the present invention provides that the use of a serpin and a Threonine protease inhibitor in a single oral composition dramatically, unexpectedly, increase the bioavailability of Exenatide. In another embodiment, the present invention provides that the use of a serpin and a Metalloprotease inhibitor in a single oral composition dramatically, unexpectedly, increase the bioavailability of a protein of the invention. In another embodiment, the present invention provides that the use of a serpin and a Metalloprotease inhibitor in a single oral composition dramatically, unexpectedly, increase the bioavailability of insulin. In another embodiment, the present invention provides that the use of a serpin and a Metalloprotease inhibitor in a single oral composition dramatically, unexpectedly, increase the bioavailability of Exenatide. In another embodiment, the present invention provides that the use of a serpin and an Aspartic protease inhibitor in a single oral composition dramatically, unexpectedly, increase the bioavailability of a protein of the invention. In another embodiment, the present invention provides that the use of a serpin and an Aspartic protease inhibitor in a single oral composition dramatically, unexpectedly, increase the bioavailability of insulin. In another embodiment, the present invention provides that the use of a serpin and an Aspartic protease inhibitor in a single oral composition dramatically, unexpectedly, increase the bioavailability of Exenatide.

In another embodiment, the present invention provides that the use of two protease inhibitors in a single oral composition dramatically, unexpectedly, increase the bioavailability of a protein of the invention. In another embodiment, the present invention provides that the use of two protease inhibitors in a single oral composition dramatically, unexpectedly, increase the bioavailability of insulin. In another embodiment, the present invention provides that the use of two protease inhibitors in a single oral composition dramatically, unexpectedly, increase the bioavailability of Exenatide. In another embodiment, the present invention provides that the use of two protease inhibitors in a single oral composition dramatically, unexpectedly, increase the bioavailability of insulin in a human subject. In another embodiment, the present invention provides that the use of two protease inhibitors in a single oral composition dramatically, unexpectedly, increase the bioavailability of Exenatide in a human subject. In another embodiment, the present invention provides that the use of two protease inhibitors in a single oral composition dramatically, unexpectedly, increase the bioavailability of a protein of the invention in a human subject.

In another embodiment, the present invention provides that the use of two protease inhibitors in a single oral composition dramatically, unexpectedly, increase the bioavailability of insulin in a human subject by at least 10%. In another embodiment, the present invention provides that the use of two protease inhibitors in a single oral composition dramatically, unexpectedly, increase the bioavailability of Exenatide in a human subject by at least 10%. In another embodiment, the present invention provides that the use of two protease inhibitors in a single oral composition dramatically, unexpectedly, increase the bioavailability of insulin in a human subject by at least 20%. In another embodiment, the present invention provides that the use of two protease inhibitors in a single oral composition dramatically, unexpectedly, increase the bioavailability of Exenatide in a human subject by at least 20%. In another embodiment, the present invention provides that the use of two protease inhibitors in a single oral composition dramatically, unexpectedly, increase the bioavailability of insulin in a human subject by at least 30%. In another embodiment, the present invention provides that the use of two protease inhibitors in a single oral composition dramatically, unexpectedly, increase the bioavailability of Exenatide in a human subject by at least 30%. In another embodiment, the present invention provides that the use of two protease inhibitors in a single oral composition dramatically, unexpectedly, increase the bioavailability of insulin in a human subject by at least 40%. In another embodiment, the present invention provides that the use of two protease inhibitors in a single oral composition dramatically, unexpectedly, increase the bioavailability of Exenatide in a human subject by at least 40%. In another embodiment, the present invention provides that the use of two protease inhibitors in a single oral composition dramatically, unexpectedly, increase the bioavailability of insulin in a human subject by at least 50%. In another embodiment, the present invention provides that the use of two protease inhibitors in a single oral composition dramatically, unexpectedly, increase the bioavailability of Exenatide in a human subject by at least 50%. In another embodiment, the present invention provides that the use of two protease inhibitors in a single oral composition dramatically, unexpectedly, increase the bioavailability of insulin in a human subject by at least 60%. In another embodiment, the present invention provides that the use of two protease inhibitors in a single oral composition dramatically, unexpectedly, increase the bioavailability of Exenatide in a human subject by at least 60%. In another embodiment, the present invention provides that the use of two protease inhibitors in a single oral composition dramatically, unexpectedly, increase the bioavailability of insulin in a human subject by at least 70%. In another embodiment, the present invention provides that the use of two protease inhibitors in a single oral composition dramatically, unexpectedly, increase the bioavailability of Exenatide in a human subject by at least 70%. In another embodiment, the present invention provides that the use of two protease inhibitors in a single oral composition dramatically, unexpectedly, increase the bio availability of insulin in a human subject by at least 80%. In another embodiment, the present invention provides that the use of two protease inhibitors in a single oral composition dramatically, unexpectedly, increase the bioavailability of Exenatide in a human subject by at least 80%. In another embodiment, the present invention provides that the use of two protease inhibitors in a single oral composition dramatically, unexpectedly, increase the bio availability of insulin in a human subject by at least 90%. In another embodiment, the present invention provides that the use of two protease inhibitors in a single oral composition dramatically, unexpectedly, increase the bioavailability of Exenatide in a human subject by at least 90%. In another embodiment, the present invention provides that the use of two protease inhibitors in a single oral composition dramatically, unexpectedly, increase the bioavailability of insulin in a human subject by at least 100%. In another embodiment, the present invention provides that the use of two protease inhibitors in a single oral composition dramatically, unexpectedly, increase the bioavailability of Exenatide in a human subject by at least 100%.

In another embodiment, the present invention provides that the use of Aprotinin and SBTI in a single oral composition dramatically, unexpectedly, increase the bioavailability of insulin in a human subject by at least 10%. In another embodiment, the present invention provides that the use of Aprotinin and SBTI in a single oral composition dramatically, unexpectedly, increase the bioavailability of insulin in a human subject by at least 20%. In another embodiment, the present invention provides that the use of Aprotinin and SBTI in a single oral composition dramatically, unexpectedly, increase the bioavailability of insulin in a human subject by at least 30%. In another embodiment, the present invention provides that the use of Aprotinin and SBTI in a single oral composition dramatically, unexpectedly, increase the bioavailability of insulin in a human subject by at least 40%. In another embodiment, the present invention provides that the use of Aprotinin and SBTI in a single oral composition dramatically, unexpectedly, increase the bioavailability of insulin in a human subject by at least 50%. In another embodiment, the present invention provides that the use of Aprotinin and SBTI in a single oral composition dramatically, unexpectedly, increase the bioavailability of insulin in a human subject by at least 60%. In another embodiment, the present invention provides that the use of Aprotinin and SBTI in a single oral composition dramatically, unexpectedly, increase the bioavailability of insulin in a human subject by at least 70%. In another embodiment, the present invention provides that the use of Aprotinin and SBTI in a single oral composition dramatically, unexpectedly, increase the bioavailability of insulin in a human subject by at least 80%. In another embodiment, the present invention provides that the use of Aprotinin and SBTI in a single oral composition dramatically, unexpectedly, increase the bioavailability of insulin in a human subject by at least 90%. In another embodiment, the present invention provides that the use of Aprotinin and SBTI in a single oral composition dramatically, unexpectedly, increase the bioavailability of insulin in a human subject by at least 100%.

In another embodiment, the present invention provides that the use of Aprotinin and SBTI in a single oral composition dramatically, unexpectedly, increase the bioavailability of Exenatide in a human subject by at least 10%. In another embodiment, the present invention provides that the use of Aprotinin and SBTI in a single oral composition dramatically, unexpectedly, increase the bioavailability of Exenatide in a human subject by at least 20%. In another embodiment, the present invention provides that the use of Aprotinin and SBTI in a single oral composition dramatically, unexpectedly, increase the bioavailability of Exenatide in a human subject by at least 30%. In another embodiment, the present invention provides that the use of Aprotinin and SBTI in a single oral composition dramatically, unexpectedly, increase the bioavailability of Exenatide in a human subject by at least 40%. In another embodiment, the present invention provides that the use of Aprotinin and SBTI in a single oral composition dramatically, unexpectedly, increase the bioavailability of Exenatide in a human subject by at least 50%. In another embodiment, the present invention provides that the use of Aprotinin and SBTI in a single oral composition dramatically, unexpectedly, increase the bioavailability of Exenatide in a human subject by at least 60%. In another embodiment, the present invention provides that the use of Aprotinin and SBTI in a single oral composition dramatically, unexpectedly, increase the bioavailability of Exenatide in a human subject by at least 70%. In another embodiment, the present invention provides that the use of Aprotinin and SBTI in a single oral composition dramatically, unexpectedly, increase the bioavailability of Exenatide in a human subject by at least 80%. In another embodiment, the present invention provides that the use of Aprotinin and SBTI in a single oral composition dramatically, unexpectedly, increase the bioavailability of Exenatide in a human subject by at least 90%. In another embodiment, the present invention provides that the use of Aprotinin and SBTI in a single oral composition dramatically, unexpectedly, increase the bioavailability of Exenatide in a human subject by at least 100%.

In another embodiment, the present invention provides that the use of two protease inhibitors in a single oral composition dramatically, unexpectedly, increase the bioavailability of a protein of the invention in a human subject by at least 10%. In another embodiment, the present invention provides that the use of two protease inhibitors in a single oral composition dramatically, unexpectedly, increase the bioavailability of a protein of the invention in a human subject by at least 20%. In another embodiment, the present invention provides that the use of two protease inhibitors in a single oral composition dramatically, unexpectedly, increase the bioavailability of a protein of the invention in a human subject by at least 30%. In another embodiment, the present invention provides that the use of two protease inhibitors in a single oral composition dramatically, unexpectedly, increase the bioavailability of a protein of the invention in a human subject by at least 40%. In another embodiment, the present invention provides that the use of two protease inhibitors in a single oral composition dramatically, unexpectedly, increase the bioavailability of a protein of the invention in a human subject by at least 50%. In another embodiment, the present invention provides that the use of two protease inhibitors in a single oral composition dramatically, unexpectedly, increase the bioavailability of a protein of the invention in a human subject by at least 60%. In another embodiment, the present invention provides that the use of two protease inhibitors in a single oral composition dramatically, unexpectedly, increase the bioavailability of a protein of the invention in a human subject by at least 70%. In another embodiment, the present invention provides that the use of two protease inhibitors in a single oral composition dramatically, unexpectedly, increase the bioavailability of a protein of the invention in a human subject by at least 80%. In another embodiment, the present invention provides that the use of two protease inhibitors in a single oral composition dramatically, unexpectedly, increase the bioavailability of a protein of the invention in a human subject by at least 90%. In another embodiment, the present invention provides that the use of two protease inhibitors in a single oral composition dramatically, unexpectedly, increase the bioavailability of a protein of the invention in a human subject by at least 100%.

In another embodiment, this invention further provides the use of sustained release dosage forms (e.g. sustained release microencapsulation) that enable the treatment frequency to be reduced to once or twice a day. In another embodiment, the insulin dosage is increased correspondingly with decreasing frequency of administration. In another embodiment, the Exenatide dosage is increased correspondingly with decreasing frequency of administration. Each type of coating, dosage form, etc, that inhibits digestion of the composition in the stomach represents a separate embodiment of the present invention.

Methods of measuring insulin levels are well known in the art. In one embodiment, levels of recombinant insulin are measuring using a human insulin radio-immunoassay (RIA) kit, e.g. the kit manufactured by. Linco Research Inc, (St. Charles, Mo.). In another embodiment, levels of C peptide are measured as well, to determine the relative contributions of endogenous and exogenous insulin to observed rises in insulin levels. In another embodiment, insulin ELISA kits are used. In another embodiment, insulin levels are measured by any other method known in the art. In another embodiment, Exenatide levels are measured by a method known in the art. Each possibility represents a separate embodiment of the present invention.

In another embodiment, a multiparticulate dosage forms is used to inhibit digestion of the composition in the stomach. In another embodiment, a multiparticulate dosage forms is used to inhibit digestion of the composition in the stomach. In another embodiment, the present invention comprises administering separate dosage forms wherein each protease inhibitor is in a separate dosage form and the protein is in an additional dosage form. In another embodiment, the present invention comprises administering separate dosage forms wherein the two protease inhibitors are in a single dosage form and the protein is in an additional dosage form.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein and at least two protease inhibitors, thereby orally administering a protein with an enzymatic activity to a subject. In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein and at least two protease inhibitors, thereby orally administering a protein with an enzymatic activity to a human subject. In another embodiment, the present invention provides a method for oral administration of insulin to a subject, whereby a substantial fraction of insulin retains its activity after absorption through an intestinal mucosal barrier of the subject, comprising administering orally to the subject a pharmaceutical composition comprising insulin and at least two protease inhibitors, thereby orally administering a protein with an enzymatic activity to a subject. In another embodiment, the present invention provides a method for oral administration of Exenatide to a subject, whereby a substantial fraction of Exenatide retains its activity after absorption through an intestinal mucosal barrier of the subject, comprising administering orally to the subject a pharmaceutical composition comprising Exenatide and at least two protease inhibitors, thereby orally administering a protein with an enzymatic activity to a subject.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein at least two protease inhibitors and an omega-3 fatty acid, thereby orally administering a protein with an enzymatic activity to a subject. In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein, at least two protease inhibitors and an omega-3 fatty acid, thereby orally administering a protein with an enzymatic activity to a human subject. In another embodiment, the present invention provides a method for oral administration of insulin to a subject, whereby a substantial fraction of insulin retains its activity after absorption through an intestinal mucosal barrier of the subject, comprising administering orally to the subject a pharmaceutical composition comprising insulin, at least two protease inhibitors and an omega-3 fatty acid, thereby orally administering a protein with an enzymatic activity to a subject. In another embodiment, the present invention provides a method for oral administration of Exenatide to a subject, whereby a substantial fraction of Exenatide retains its activity after absorption through an intestinal mucosal barrier of the subject, comprising administering orally to the subject a pharmaceutical composition comprising Exenatide, at least two protease inhibitors and an omega-3 fatty acid, thereby orally administering a protein with an enzymatic activity to a subject.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein at least two protease inhibitors, an omega-3 fatty acid, and Na-EDTA, thereby orally administering a protein with an enzymatic activity to a subject. In another embodiment, the present invention provides a method for oral administration of a protein with an enzymatic activity to a subject, whereby a substantial fraction of the protein retains the enzymatic activity after absorption through an intestinal mucosal bather of the subject, comprising administering orally to the subject a pharmaceutical composition comprising the protein, at least two protease inhibitors, an omega-3 fatty acid, and Na-EDTA, thereby orally administering a protein with an enzymatic activity to a human subject. In another embodiment, the present invention provides a method for oral administration of insulin to a subject, whereby a substantial fraction of insulin retains its activity after absorption through an intestinal mucosal bather of the subject, comprising administering orally to the subject a pharmaceutical composition comprising insulin, at least two protease inhibitors, an omega-3 fatty acid, and Na-EDTA, thereby orally administering a protein with an enzymatic activity to a subject. In another embodiment, the present invention provides a method for oral administration of Exenatide to a subject, whereby a substantial fraction of Exenatide retains its activity after absorption through an intestinal mucosal bather of the subject, comprising administering orally to the subject a pharmaceutical composition comprising Exenatide, at least two protease inhibitors, an omega-3 fatty acid, and Na-EDTA, thereby orally administering a protein with an enzymatic activity to a subject.

In another embodiment, the present invention provides a method for oral administration of a protein with an enzymatic activity to a subject, whereby a substantial fraction of the protein retains the enzymatic activity after absorption through an intestinal mucosal bather of the subject, comprising administering orally to the subject a pharmaceutical composition comprising the protein at least two protease inhibitors and Na-EDTA, thereby orally administering a protein with an enzymatic activity to a subject. In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein, at least two protease inhibitors and Na-EDTA, thereby orally administering a protein with an enzymatic activity to a human subject. In another embodiment, the present invention provides a method for oral administration of insulin to a subject, whereby a substantial fraction of insulin retains its activity after absorption through an intestinal mucosal barrier of the subject, comprising administering orally to the subject a pharmaceutical composition comprising insulin, at least two protease inhibitors and Na-EDTA, thereby orally administering a protein with an enzymatic activity to a subject. In another embodiment, the present invention provides a method for oral administration of Exenatide to a subject, whereby a substantial fraction of Exenatide retains its activity after absorption through an intestinal mucosal barrier of the subject, comprising administering orally to the subject a pharmaceutical composition comprising Exenatide, at least two protease inhibitors and Na-EDTA, thereby orally administering a protein with an enzymatic activity to a subject.

In another embodiment, the present invention provides a method for treating diabetes mellitus in a human subject, comprising administering orally to the subject a pharmaceutical composition comprising an insulin and at least two protease inhibitors, thereby treating diabetes mellitus. In another embodiment, the present invention provides a method for treating diabetes mellitus in a human subject, comprising administering orally to the subject a pharmaceutical composition comprising an insulin and at least two protease inhibitors, thereby treating diabetes mellitus.

In another embodiment, the present invention provides a method for treating diabetes mellitus in a human subject, comprising administering orally to the subject a pharmaceutical composition comprising an insulin, omega-3 fatty acid, and at least two protease inhibitors, thereby treating diabetes mellitus. In another embodiment, the present invention provides a method for treating diabetes mellitus in a human subject, comprising administering orally to the subject a pharmaceutical composition comprising an insulin, omega-3 fatty acid, and at least two protease inhibitors, thereby treating diabetes mellitus.

In another embodiment, the present invention provides a method for treating diabetes mellitus in a human subject, comprising administering orally to the subject a pharmaceutical composition comprising an insulin, Na-EDTA, omega-3 fatty acid, and at least two protease inhibitors, thereby treating diabetes mellitus. In another embodiment, the present invention provides a method for treating diabetes mellitus in a human subject, comprising administering orally to the subject a pharmaceutical composition comprising an insulin, Na-EDTA, omega-3 fatty acid, and at least two protease inhibitors, thereby treating diabetes mellitus.

In another embodiment, the present invention provides a method for treating diabetes mellitus in a human subject, comprising administering orally to the subject a pharmaceutical composition comprising a Exenatide and at least two protease inhibitors, thereby treating diabetes mellitus. In another embodiment, the present invention provides a method for treating diabetes mellitus in a human subject, comprising administering orally to the subject a pharmaceutical composition comprising a Exenatide and at least two protease inhibitors, thereby treating diabetes mellitus.

In another embodiment, the present invention provides a method for treating diabetes mellitus in a human subject, comprising administering orally to the subject a pharmaceutical composition comprising a Exenatide, omega-3 fatty acid, and at least two protease inhibitors, thereby treating diabetes mellitus. In another embodiment, the present invention provides a method for treating diabetes mellitus in a human subject, comprising administering orally to the subject a pharmaceutical composition comprising a Exenatide, omega-3 fatty acid, and at least two protease inhibitors, thereby treating diabetes mellitus.

In another embodiment, the present invention provides a method for treating diabetes mellitus in a human subject, comprising administering orally to the subject a pharmaceutical composition comprising a Exenatide, Na-EDTA, omega-3 fatty acid, and at least two protease inhibitors, thereby treating diabetes mellitus. In another embodiment, the present invention provides a method for treating diabetes mellitus in a human subject, comprising administering orally to the subject a pharmaceutical composition comprising a Exenatide, Na-EDTA, omega-3 fatty acid, and at least two protease inhibitors, thereby treating diabetes mellitus.

In one embodiment, the diabetes mellitus is Type I diabetes. In another embodiment, the diabetes mellitus is Type II diabetes. In another embodiment, the diabetes mellitus is insulin-dependent diabetes. In another embodiment, the diabetes mellitus is non-insulin-dependent diabetes. In another embodiment, the diabetes mellitus is any other type of diabetes known in the art. Each possibility represents a separate embodiment of the present invention.

In one embodiment, three treatments a day of the insulin composition are administered. In another embodiment, two treatments a day are administered. In another embodiment, four treatments a day are administered. In another embodiment, one treatment a day is administered. In another embodiment, more than four treatments a day are administered. Each possibility represents a separate embodiment of the present invention.

Any of the methods of the present invention may utilize, in various embodiments, any of the compositions of the present invention.

In another embodiment, the present invention provides a composition for oral administration of insulin, comprising an insulin protein and at least two protease inhibitors, whereby a substantial fraction of the insulin retains the enzymatic activity after absorption through an intestinal mucosal barrier of a human subject. In another embodiment, the present invention provides a composition for oral administration of Exenatide, comprising an insulin protein and at least two protease inhibitors, whereby a substantial fraction of the Exenatide retains the enzymatic activity after absorption through an intestinal mucosal bather of a human subject. In one embodiment, the present invention provides a composition for oral administration of a protein, comprising a protein and at least two protease inhibitors, whereby a substantial fraction of the protein retains the enzymatic activity after absorption through an intestinal mucosal barrier of the subject.

In one embodiment, the present invention provides the use of a protein and at least two protease inhibitors in the manufacture of a medicament for oral administration of a protein with an enzymatic activity to a subject, whereby a substantial fraction of the protein retains the enzymatic activity after absorption through an intestinal mucosal barrier of the subject. In one embodiment, the present invention provides the use of a protein, at least two protease inhibitors, and an omega-3 fatty acid in the manufacture of a medicament for oral administration of a protein with an enzymatic activity to a subject, whereby a substantial fraction of the protein retains the enzymatic activity after absorption through an intestinal mucosal barrier of the subject. In one embodiment, the present invention provides the use of a protein, at least two protease inhibitors, Na-EDTA, and an omega-3 fatty acid in the manufacture of a medicament for oral administration of a protein with an enzymatic activity to a subject, whereby a substantial fraction of the protein retains the enzymatic activity after absorption through an intestinal mucosal barrier of the subject.

In one embodiment, the present invention provides the use of an insulin protein and at least two protease inhibitors in the manufacture of a medicament for treating diabetes mellitus in a subject. In one embodiment, the present invention provides the use of an insulin protein, at least two protease inhibitors, and an omega-3 fatty acid in the manufacture of a medicament for treating diabetes mellitus in a subject. In one embodiment, the present invention provides the use of an insulin protein, at least two protease inhibitors, Na-EDTA, and an omega-3 fatty acid in the manufacture of a medicament for treating diabetes mellitus in a subject.

In one embodiment, the present invention provides the use of a Exenatide protein and at least two protease inhibitors in the manufacture of a medicament for treating diabetes mellitus in a subject. In one embodiment, the present invention provides the use of a Exenatide protein, at least two protease inhibitors, and an omega-3 fatty acid in the manufacture of a medicament for treating diabetes mellitus in a subject. In one embodiment, the present invention provides the use of a Exenatide protein, at least two protease inhibitors, Na-EDTA, and an omega-3 fatty acid in the manufacture of a medicament for treating diabetes mellitus in a subject.

In one embodiment, methods and compositions of the present invention have the advantage of more closely mimicking physiological insulin secretion by the pancreas. When insulin is secreted into the portal vein, the liver is exposed to a greater insulin concentration than peripheral tissues. Similarly, insulin administered according to the present invention reaches the intestine and is absorbed in the body through the intestine and through the portal system to the liver. This absorption route thus resembles the physiological secretion of insulin by the pancreas, enabling, in this embodiment, delicate control of the blood glucose level and the metabolic activities of the liver and the peripheral organs controlled by insulin. By contrast, when insulin is administered to insulin-deficient diabetic patients via the peripheral venous system, the concentration of insulin in the portal vein is similar to that in the peripheral circulation, resulting in hypoinsulinemia in the portal vein and the liver and hyperinsulinemia in the peripheral venous system. This leads, in one embodiment, to an abnormal pattern of glucose disposal.

In another embodiment, different constituents of compositions of the present composition are absorbed at different rates from the intestinal lumen into the blood stream. The absorption of the bile acid, in one embodiment, is significantly faster than the absorption of insulin.

For this reason, in another embodiment, a drug regimen involving ingestion of a pair of pills at spaced intervals, e.g., a second pill containing a higher concentration of enhancer is taken at a defined interval (e.g. 30 minutes) after the first pill. In another embodiment, certain of the constituents are microencapsulated to enhance the absorption of the insulin into the system. In another embodiment, certain of the constituents are microencapsulated to enhance the absorption of the Exenatide into the system.

In one embodiment, a treatment protocol of the present invention is therapeutic. In another embodiment, the protocol is prophylactic. Each possibility represents a separate embodiment of the present invention.

In another embodiment, solid carriers/diluents for use in methods and compositions of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In some embodiments, the dosage forms of the present invention are formulated to achieve an immediate release profile, an extended release profile, or a delayed release profile. In some embodiments, the release profile of the composition is determined by using specific excipients that serve for example as binders, disintegrants, fillers, or coating materials. In one embodiment, the composition will be formulated to achieve a particular release profile as known to one skilled in the art.

In one embodiment, the composition is formulated as an oral dosage form. In one embodiment, the composition is a solid oral dosage form comprising tablets, chewable tablets, or capsules. In one embodiment the capsules are soft gelatin capsules. In another embodiment, capsules as described herein are hard-shelled capsules. In another embodiment, capsules as described herein are soft-shelled capsules. In another embodiment, capsules as described herein are made from gelatine. In another embodiment, capsules as described herein are made from plant-based gelling substances like carrageenans and modified forms of starch and cellulose.

In other embodiments, controlled- or sustained-release coatings utilized in methods and compositions of the present invention include formulation in lipophilic depots (e.g. fatty acids, waxes, oils).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. In another embodiment, particulate compositions of the active ingredients are coated with polymers (e.g. poloxamers or poloxamines)

In another embodiment, the compositions containing the insulin and omega-3 fatty acid are delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid). In another embodiment, the compositions containing the Exenatide and omega-3 fatty acid are delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the active ingredients of compositions of the present invention are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

Each of the above additives, excipients, formulations and methods of administration represents a separate embodiment of the present invention.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease.

EXPERIMENTAL DETAILS SECTION

Example 1: Capsules Comprising a Protein and a Combination of Protease Inhibitors Materials and Experimental Methods Formulation 4 days prior to dosing, formulation were prepared containing: (1) 8 mg insulin, 150 mg EDTA, 125 mg SBTI in 1 ml fish oil in a soft-gel capsule (SwissCup), (2). 8 mg insulin, 150 mg EDTA, 150000 KIU Aprotinin in 1 ml fish oil in a soft-gel capsule (SwissCup), (3) 8 mg insulin, 150 mg EDTA, 150000 KIU Aprotinin, 125 mg SBTI in 1 ml fish oil in a soft-gel capsule (SwissCup). The formulations were stored in the refrigerator (4° C.) until dosing.

Results

In the next experiment, the formulations as describes in the "Formulation" section were orally consumed by healthy human subjects. As shown in FIG. 1, blood glucose levels were significantly reduced and more stable in human subjects treated with formulation (3) (8 mg insulin, 150 mg EDTA, 150000 KIU Aprotinin, 125 mg SBTI in 1 ml fish oil in a soft-gel capsule (SwissCup). These results also suggest that the two protease inhibitors in formulation (3) had a synergistic effect in lowering blood glucose levels.

It should be emphasized that no differences in the reduction of blood glucose levels were observed in a previous experiment in dogs treated with the same formulations comprising a single protease inhibitor (formulations 1 or 2, SBTI or Aprotinin) or a formulation that comprises both SBTI and Aprotinin (formulation 3). Thus, the results regarding the reduction in blood glucose levels with insulin and a combination of protease inhibitors was unexpected.

Figure 1D:
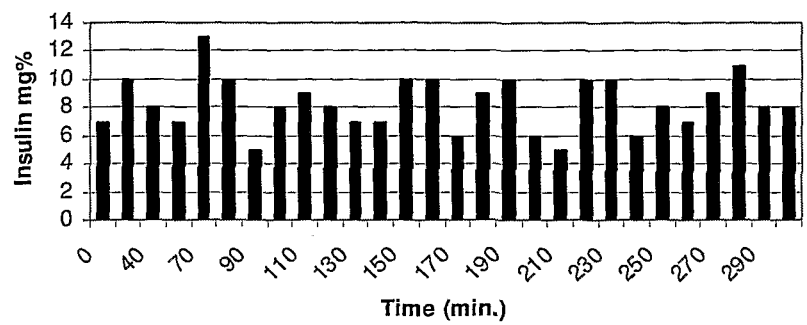
Figure 1E:
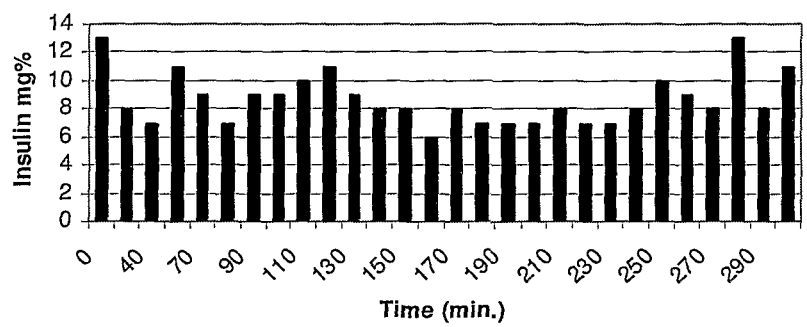
Figure 1F:
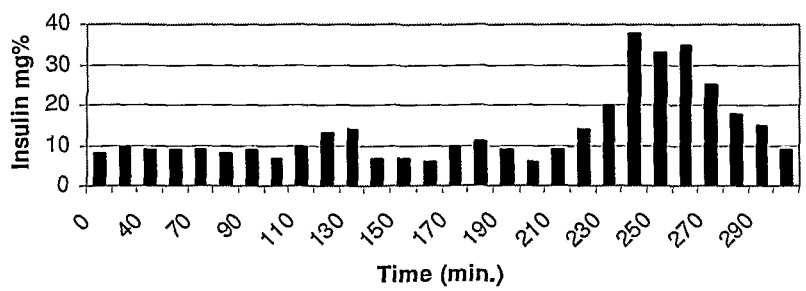

Furthermore, as shown in FIG. 1D-F, total blood insulin was significantly higher especially between 220-300 minutes in human subjects treated with formulation (3) (8 mg insulin, 150 mg EDTA, 150000 KIU Aprotinin, 125 mg SBTI in 1 ml fish oil in a soft-gel capsule (SwissCup). These results also suggest that the two protease inhibitors in formulation (3) had a synergistic effect in stabling insulin levels.

Figure 1G:
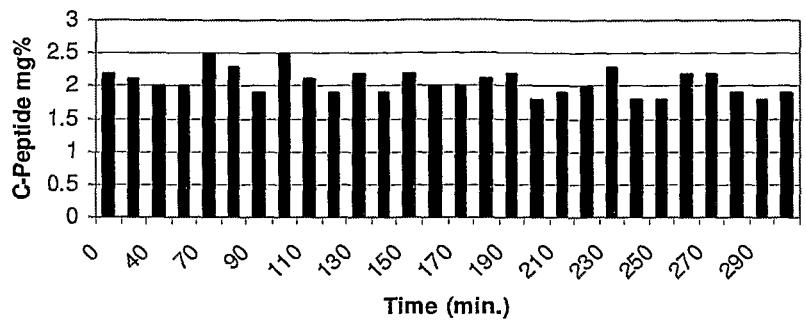
Figure 1H:
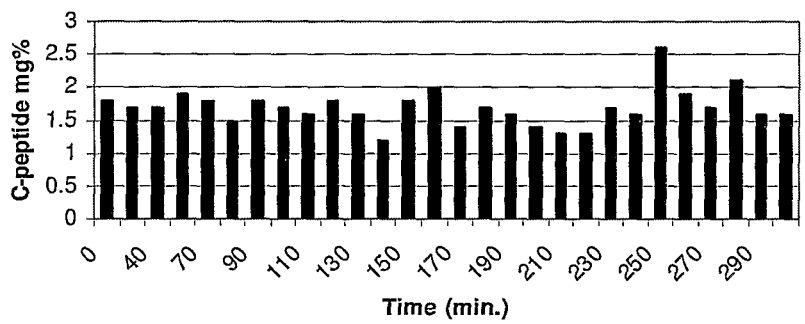
Figure 1I:
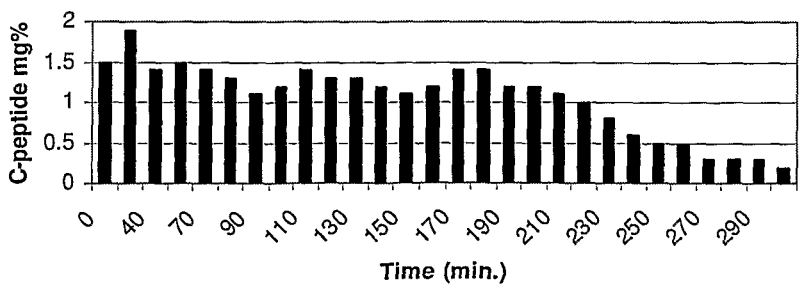

As shown in FIG. 1G-I, blood C-peptide levels were significantly reduced in human subjects treated with formulation (3) (8 mg insulin, 150 mg EDTA, 150000 KIU Aprotinin, 125 mg SBTI in 1 ml fish oil in a soft-gel capsule (SwissCup). These results also suggest that the two protease inhibitors in formulation (3) had a synergistic effect in lowering blood C-peptide levels.

In a similar experiment in healthy humans, formulations comprising: (1) 150 mg EDTA, 24 mg Aprotinin, 75 mg BBI, and 10 mg insulin; (2) 150 mg EDTA, 24 mg Aprotinin, 75 mg Kunitz, and 12 mg insulin; and (3) 150 mg of EDTA, 24 mg Aprotinin, 75 mg SBTI, and 8 mg of insulin were found to be effective in lowering blood glucose levels and maintaining sufficient blood insulin levels for over 3 hours after a meal.

It should be emphasized that no differences in the reduction of C-peptide levels were observed in a previous experiment in dogs treated with the same formulations comprising a single protease inhibitor (formulations 1 or 2, SBTI or Aprotinin) or a formulation that comprises both SBTI and Aprotinin (formulation 3). Thus, the results regarding the reduction in blood C-peptide levels with insulin and a combination of protease inhibitors was unexpected.

The above described formulations are also active with 0.5 ml fish oil both in dogs and humans. Dogs do not react to Aprotinin. Therefore in dogs the reduction in blood glucose with SBTI alone was equivalent to the reduction in blood glucose with both Aprotinin and SBTI. Moreover, a formulation comprising insulin and Aprotinin but not SBTI did not reduce blood glucose in dogs.

Example 2: Optimization of Source of Omega-3 Fatty Acids

Various omega-3 fatty acids or sources of omega-3 fatty acids (e.g. those listed above in the specification) are compared for their ability to preserve insulin following oral administration in methods and compositions of the present invention. Insulin tablets or capsules are formulated as described in the above Examples, except that the insulin is dissolved in the alternate source instead of in fish oil. The most effective source of omega-3 fatty acids is used in subsequent Examples.

Example 3: Optimization of Protease Inhibitors

Various protease inhibitors (either non-toxic or having an acceptable toxicity profile; e.g. those listed above in the specification) are compared for their ability to preserve insulin following oral administration in methods and compositions of the present invention. Insulin and/or Exenatide tablets or capsules are formulated as described in the above Examples, except that the alternate protease inhibitors are substituted for SBTI and/or Aprotinin. Amounts of the protease inhibitors are also varied, to determine the optimal amounts. The most effective protease inhibitor/amount is used in subsequent Examples.

Example 4: Optimization of Enhancer

Various enhancers (e.g. those listed above in the specification) are compared for their ability to facilitate absorption of insulin following oral administration in methods and compositions of the present invention. Insulin tablets or capsules are formulated as described in the above Examples, except that the alternate enhancers are substituted for EDTA. Amounts of the enhancers are also varied, to determine the optimal amounts. The most effective enhancer/amount is used in subsequent experiments.

Example 5: Optimization of Type and Amount of Insulin

Various types and amounts of insulin e.g. those listed above in the specification) are compared for their ability to regulate blood sugar in methods and compositions of the present invention. Insulin tablets or capsules are formulated as described in the above Examples, except that the type and amount of insulin is varied. The most effective type/amount of insulin is used in clinical trials.

What is claimed is:

1. An oral pharmaceutical composition comprising a protein and two protease inhibitors in a pharmaceutically acceptable formulation, wherein said protein is insulin, Exenatide, somatotropin, insulin growth factor-I, an oxidoreductase, a transferase, a hydrolase, a lyase, an isomerase, a ligase, an annexin, an ATP-binding cassette transporter, hemoglobin, an ATPase, a calcium channel, a potassium channel, a sodium channel, a solute carrier, an albumin, lactoglobulin, casein, ovomucin, ferritin, phosvitin, lactoferrin, vitellogenin, amyloid, collagen, elastin, fibrillin or glucagon, wherein said protease inhibitors consist of Soybean Trypsin Inhibitor (SBTI) and aprotinin, wherein said protease inhibitors increase the bioavailability of said protein when the composition is administered orally to a subject and wherein the oral pharmaceutical composition comprises a pharmaceutically acceptable carrier.

2. The oral pharmaceutical composition of claim 1, wherein said protein is insulin.

3. The oral pharmaceutical composition of claim 1, wherein said protein is Exenatide.

4. The oral pharmaceutical composition of claim 1, wherein said protein is a recombinant protein.

5. The oral pharmaceutical composition of claim 1, further comprising an omega-3 fatty acid.

6. The oral pharmaceutical composition of claim 5, wherein said omega-3 fatty acid is derived from fish oil.

7. The oral pharmaceutical composition of claim 1, further comprising a substance that enhances absorption of said protein through an intestinal mucosal barrier.

8. The oral pharmaceutical composition of claim 7, wherein said substance is EDTA or a salt thereof.

9. The oral pharmaceutical composition of claim 7, wherein said substance is a bile acid or alkali metal salt thereof.

10. The oral pharmaceutical composition of claim 1, further comprising a coating, that inhibits digestion of said oral pharmaceutical composition in a stomach of a subject.

11. The oral pharmaceutical composition of claim 10, wherein said coating is an enteric coating.

12. The oral pharmaceutical composition of claim 1, further comprising fish oil.

13. The oral pharmaceutical composition of claim 1, further comprising a gelatin coating.

14. The oral pharmaceutical composition of claim 1, wherein the presence of said protease inhibitors increases the bioavailability of said protein in a human subject.

15. The oral pharmaceutical composition of claim 2, wherein said protein is glucagon.

16. The oral pharmaceutical composition of claim 1, wherein said protein is said somatotropin or insulin growth factor-I.

17. The oral pharmaceutical composition of claim 1, wherein said protein is said oxidoreductase, transferase, hydrolase, lyase, isomerase or ligase.

18. The oral pharmaceutical composition of claim 1, wherein said protein is said annexin, ATP-binding cassette transporter, hemoglobin, ATPase, calcium channel, potassium channel, sodium channel or solute carrier.

19. The oral pharmaceutical composition of claim 1, wherein said storage protein is said albumin, lactoglobulin, casein, ovomucin, ferritin, phosvitin, lactoferrin, or vitellogenin.

20. The oral pharmaceutical composition of claim 1, wherein said protein is said amyloid, collagen, elastin or fibrillin.

21. An oral pharmaceutical composition comprising insulin and two protease inhibitors in a pharmaceutically acceptable formulation, wherein said protease inhibitors consist of Soybean Trypsin Inhibitor (SBTI) and aprotinin, wherein said protease inhibitors increase the bioavailability of said insulin when the composition is administered orally to a human subject and wherein the oral pharmaceutical composition comprises a pharmaceutically acceptable carrier.

22. The oral pharmaceutical composition of claim 21, further comprising an omega-3 fatty acid.

23. The oral pharmaceutical composition of claim 22, wherein said omega-3 fatty acid is derived from fish oil.

24. The oral pharmaceutical composition of claim 21, further comprising a substance that enhances absorption of said protein through an intestinal mucosal barrier.

25. The oral pharmaceutical composition of claim 24, wherein said substance is EDTA or a salt thereof.

26. The oral pharmaceutical composition of claim 24, wherein said substance is a bile acid or alkali metal salt thereof.

27. The oral pharmaceutical composition of claim 21, further comprising a coating that inhibits digestion of said oral pharmaceutical composition in a stomach of a subject.

28. The oral pharmaceutical composition of claim 27, wherein said coating is an enteric coating.

29. An oral pharmaceutical composition comprising Exenatide and two protease inhibitors in a pharmaceutically acceptable formulation, wherein said protease inhibitors consist of Soybean Trypsin Inhibitor (SBTI) and aprotinin, wherein said protease inhibitors increase the bioavailability of said Exenatide when the composition is administered orally to a human subject and wherein the oral pharmaceutical composition comprises a pharmaceutically acceptable carrier.

30. The oral pharmaceutical composition of claim 29, further comprising an omega-3 fatty acid.

31. The oral pharmaceutical composition of claim 30, wherein said omega-3 fatty acid is derived from fish oil.

32. The oral pharmaceutical composition of claim 29, further comprising a substance that enhances absorption of said protein through an intestinal mucosal barrier.

33. The oral pharmaceutical composition of claim 32, wherein said substance is EDTA or a salt thereof.

34. The oral pharmaceutical composition of claim 32, wherein said substance is a bile acid or alkali metal salt thereof.

35. The oral pharmaceutical composition of claim 29, further comprising a coating that inhibits digestion of said oral pharmaceutical composition in a stomach of a subject.

36. The oral pharmaceutical composition of claim 35, wherein said coating is an enteric coating.

37. An oral pharmaceutical composition comprising glucagon and two protease inhibitors in a pharmaceutically acceptable formulation, wherein said protease inhibitors consist of Soybean Trypsin Inhibitor (SBTI) and aprotinin, wherein said protease inhibitors increase the bioavailability of said glucagon when the composition is administered orally to a human subject and wherein the oral pharmaceutical composition comprises a pharmaceutically acceptable carrier.

38. The oral pharmaceutical composition of claim 37, further comprising an omega-3 fatty acid.

39. The oral pharmaceutical composition of claim 38, wherein said omega-3 fatty acid is derived from fish oil.

40. The oral pharmaceutical composition of claim 37, further comprising a substance that enhances absorption of said protein through an intestinal mucosal barrier.

41. The oral pharmaceutical composition of claim 40, wherein said substance is EDTA or a salt thereof.

42. The oral pharmaceutical composition of claim 41, wherein said substance is a bile acid or alkali metal salt thereof.

43. The oral pharmaceutical composition of claim 37, further comprising a coating that inhibits digestion of said oral pharmaceutical composition in a stomach of a subject.

44. The oral pharmaceutical composition of claim 43, wherein said coating is an enteric coating.

45. The oral pharmaceutical composition of claim 1, comprising a protein and two protease inhibitors in a pharmaceutically acceptable formulation, wherein said protein has a molecular weight of up to 10,000 Daltons, wherein said protease inhibitors consist of Soybean Trypsin Inhibitor (SBTI) and aprotinin, and wherein said protease inhibitors increase the bioavailability of said protein when the composition is administered orally to a subject.

46. The oral pharmaceutical composition of claim 45, wherein the protein has a molecular weight of up to 6,000 Daltons.

* * * * *

UNITED STATES PATENT AND TRADEMARK OFFICE
CERTIFICATE OF CORRECTION

PATENT NO. : 10,058,593 B2
APPLICATION NO. : 12/934754
DATED : August 28, 2018
INVENTOR(S) : Miriam Kidron Page 1 of 1

It is certified that error appears in the above-identified patent and that said Letters Patent is hereby corrected as shown below:

In the Claims

In Column 29, Line 66, (Line 1 in Claim 15), replace "claim 2" with -- claim 1 --, therefor.

Signed and Sealed this
Twenty-eighth Day of May, 2019

Andrei Iancu
*Director of the United States Patent and Trademark Office*